United States Patent
Burrows-Ownbey et al.

(10) Patent No.: US 12,318,312 B2
(45) Date of Patent: Jun. 3, 2025

(54) SURGICAL INSTRUMENT FOR OPERATING SPINAL IMPLANT SYSTEM WITH DUAL AXIS ADJUSTABILITY AND METHOD OF OPERATING SAME

(71) Applicant: Adcura, Inc., Eden Prairie, MN (US)

(72) Inventors: Robyn Burrows-Ownbey, Elmdale, KS (US); Andrew Rogers, Deephaven, MN (US); Eric Blossey, Denver, CO (US)

(73) Assignee: Adcura, Inc., Eden Prairie, MN (US)

( * ) Notice: Subject to any disclaimer, the term of this patent is extended or adjusted under 35 U.S.C. 154(b) by 0 days.

(21) Appl. No.: 18/297,816

(22) Filed: Apr. 10, 2023

(65) Prior Publication Data

US 2023/0240863 A1    Aug. 3, 2023

Related U.S. Application Data

(62) Division of application No. 17/028,679, filed on Sep. 22, 2020, now Pat. No. 11,648,132.

(Continued)

(51) Int. Cl.
*A61F 2/46* (2006.01)
*A61F 2/44* (2006.01)

(52) U.S. Cl.
CPC ..... *A61F 2/4611* (2013.01); *A61F 2002/4629* (2013.01)

(58) Field of Classification Search
CPC .......... A61F 2/4611; A61F 2/44; A61F 2/447; A61F 2002/4629

(Continued)

(56) References Cited

U.S. PATENT DOCUMENTS

| 4,453,434 A | 6/1984 | Lissy |
| 4,515,043 A | 5/1985 | Gray |

(Continued)

FOREIGN PATENT DOCUMENTS

| DE | 102009011563 A1 | 9/2010 | |
| WO | 2019022976 A | 1/2019 | |
| WO | WO-2019022976 A1 * | 1/2019 | ........... A61F 2/4455 |

OTHER PUBLICATIONS

PCT, International Search Report and Written Opinion of International Searching Authority in PCT/US2020/052028, Feb. 5, 2021, 8 pages.

(Continued)

*Primary Examiner* — Jessica Weiss
(74) *Attorney, Agent, or Firm* — Adcura IP

(57) ABSTRACT

A surgical instrument includes a chassis, a first driving shaft, a first measuring mechanism, a second measuring mechanism, and a first handle. The chassis defines a first channel and a second channel each extending from a proximal end to a distal end. The first measuring mechanism corresponds to rotation in the first channel. The second measuring mechanism corresponds to rotation in the second channel. The first driving shaft is operable to be inserted into the first channel, engaging with the first measuring mechanism. The first driving shaft has an end portion configured to engage and drive a first adjustable feature and/or a second adjustable feature on a work-piece. The handle is operable to be releasably attached to the first driving shaft for applying torque or operable to remove the first driving shaft from the first channel.

10 Claims, 27 Drawing Sheets

Related U.S. Application Data

(60) Provisional application No. 62/928,927, filed on Oct. 31, 2019, provisional application No. 62/905,052, filed on Sep. 24, 2019.

(58) Field of Classification Search
USPC .................. 623/17.11–17.16; 606/99–100
See application file for complete search history.

(56) References Cited

U.S. PATENT DOCUMENTS

| | | | |
|---|---|---|---|
| 5,572,905 A | 11/1996 | Cook, Jr. | |
| 5,700,268 A | 12/1997 | Bertin | |
| 6,641,614 B1* | 11/2003 | Wagner | A61F 2/4455 |
| | | | 623/17.15 |
| 9,889,019 B2* | 2/2018 | Rogers | A61F 2/4455 |
| 10,188,527 B2* | 1/2019 | Rogers | A61F 2/4611 |
| 2004/0254644 A1 | 12/2004 | Taylor | |
| 2007/0123905 A1* | 5/2007 | Schneid | A61F 2/4425 |
| | | | 606/99 |
| 2007/0225726 A1* | 9/2007 | Dye | A61F 2/4465 |
| | | | 606/99 |
| 2008/0021558 A1 | 1/2008 | Thramann | |
| 2008/0269756 A1* | 10/2008 | Tomko | A61B 17/1757 |
| | | | 606/86 R |
| 2010/0160984 A1 | 6/2010 | Berry et al. | |
| 2010/0168862 A1 | 7/2010 | Edie | |
| 2010/0292742 A1 | 11/2010 | Stad | |
| 2012/0116466 A1* | 5/2012 | Dinville | A61F 2/4611 |
| | | | 606/86 A |
| 2012/0158071 A1* | 6/2012 | Jimenez | A61F 2/447 |
| | | | 606/86 A |
| 2014/0013903 A1 | 1/2014 | Singh Sidhu | |
| 2015/0351925 A1 | 12/2015 | Emerick et al. | |
| 2016/0089247 A1 | 3/2016 | Nichols et al. | |
| 2018/0000606 A1* | 1/2018 | Hessler | A61F 2/447 |
| 2018/0125677 A1* | 5/2018 | Burrows-Ownbey | |
| | | | A61F 2/447 |
| 2020/0015985 A1 | 1/2020 | Rogers et al. | |
| 2020/0078190 A1* | 3/2020 | Rogers | A61F 2/4455 |

OTHER PUBLICATIONS

Taiwanese Patent Office, Office Action in PCT/US2020/052028, Jan. 11, 2024 pages.

* cited by examiner

480

480

OR

- THE DASH ARROWS INDICATE MOVEMENT OF THE TAPERED SCREWS UP THE RISER ELEMENTS OF THE OUTER SHELL TRACKING.
- THE BLACK ARROWS INDICATE AN OUTER AXIAL LOAD GENERATED BY THE DEVICE.

SURGICAL INSTRUMENT FOR OPERATING SPINAL IMPLANT SYSTEM WITH DUAL AXIS ADJUSTABILITY AND METHOD OF OPERATING SAME

CROSS-REFERENCE TO RELATED APPLICATIONS

This application is a division of U.S. application Ser. No. 17/028,679 filed Sep. 22, 2020 entitled "Surgical Instrument for Operating Spinal Implant System with Dual Axis Adjustability and Method of Operating Same," which claims priority to U.S. provisional patent application Nos. 62/905,052 filed Sep. 24, 2019, and 62/928,927 filed Oct. 31, 2019 both entitled "Surgical Instrument for Operating Spinal Implant System with Dual Axis Adjustability and Method of Operating Same," the disclosures of all of which are hereby incorporated by reference in their entirety.

TECHNICAL FIELD

This disclosure relates generally to surgical procedures and apparatuses for treating spinal diseases. In particular, various embodiments of a surgical instrument for inserting and operating expandable and adjustable lordosis interbody fusion systems and methods of operating same are described.

BACKGROUND

Spinal fusion is a surgical procedure to correct problems relating to the human spine. It generally involves removing damaged disc and bone from between adjacent vertebrae and inserting bone graft material that promotes bone growth. As the bone grows, the adjacent vertebrae join, or fuse, together. Fusing the bones together can help make that particular area of the spine more stable and help reduce problems related to nerve irritation at the site of the fusion. Fusions can be done at one or more segments of the spine.

In an interbody fusion procedure, the nucleus pulposus and/or the annulus fibrosus that compose the intervertebral disc at the point of damage are removed and an implant device is placed in the disc space to restore the distance between adjacent vertebrae to that of a proper condition. Surgical approaches to implement interbody fusion vary, and access to the patient's vertebral column can be made through the abdomen or back. One other surgical method for accomplishing lumbar spinal fusion in a less invasive way involves accessing the vertebral column through a small incision on the side of the body. This procedure is known as lateral lumbar interbody fusion.

Conventionally, once the intervertebral disc is removed from the body, the surgeon typically forces different trial implants between the vertebral endplates of the specific region to determine the appropriate size of the implant for maintaining a desired distance between the adjacent vertebrae. Another consideration is to maintain the natural angle between the vertebrae to accommodate the natural curvature of the spine. Therefore, during selection of an implant device for implantation, both the intervertebral disc height and spinal curve must be considered. Prior art fusion devices are often pre-configured to have top and bottom surfaces angles to one another to accommodate the natural curvature of the spine. However, it is usually unlikely that these values can be determined precisely prior to the operation.

SUMMARY OF THE DISCLOSURE

An embodiment of a surgical instrument includes a chassis, a first tubular sleeve and a second tubular sleeve releasably attached to the chassis, a first driving shaft, and a first handle operable to be releasably attached to the first driving shaft for applying torque. The chassis has a proximal end and a distal end and defines a first channel and a second channel each extending from the proximal end to the distal end. The first tubular sleeve is releasably attached to the first channel at the distal end of the chassis. The second tubular sleeve is releasably attached to the second channel at the distal end of the chassis. Each of the first and second tubular sleeves has an end portion configured to releasably connect to a work-piece at a first site and a second site of the work-piece respectively. The first driving shaft is operable to be inserted into the first channel from the proximal end of the chassis and into the first tubular sleeve. The first driving shaft has an end portion configured to engage and drive the work-piece. The first handle is operable to be releasably attached to the first driving shaft for applying torque.

An embodiment of the surgical instrument includes a chassis, a first measuring mechanism and a second measuring mechanism on the chassis, a first driving shaft, and a first handle operable to be releasably attached to the first driving shaft for applying torque. The chassis defines a first channel and a second channel, each extending from a proximal end to a distal end. The first measuring mechanism corresponds to rotation in the first channel and the second measuring mechanism corresponds to rotation in the second channel. The first driving shaft is operable to be inserted into the first channel from the proximal end of the chassis and engage with the first measuring mechanism. The first handle is operable to be releasably attached to the first driving shaft for applying torque or to remove the first driving shaft from the first channel.

An embodiment of a spinal interbody fusion system includes an implant device and an insertion tool. The implant device includes a housing having a first shell member and a second shell member, a first driving mechanism operable to expand and/or contract the first and second shell members from a first lateral side of the housing, and a second driving mechanism operable to expand and/or contract the first and second shell members from a second lateral side of the housing. The insertion tool includes a chassis, a first tubular sleeve and a second tubular sleeve releasably attached to the chassis, a first driving shaft, and a first handle. The chassis has a proximal end and a distal end and defines a first channel and a second channel each extending from the proximal end to the distal end. The first tubular sleeve is releasably attached to the first channel at the distal end of the chassis. The second tubular sleeve is releasably attached to the second channel at the distal end of the chassis. Each of the first and second tubular sleeves has an end portion configured to releasably connect with the first and second driving mechanisms of the implant device respectively. The first driving shaft is operable to be inserted into the first channel from the proximal end of the chassis and into the first tubular sleeve. The first driving shaft has an end portion configured to engage with the first driving mechanism of the implant device. The first handle is operable to be releasably attached to the first driving shaft for applying torque, thereby allowing the first driving shaft to drive the first driving mechanism of the implant device to effect expansion and/or contraction of the first and second shell members from the first lateral side of the housing of the implant device.

An embodiment of a spinal interbody fusion system includes an implant device and an insertion tool. The implant device includes a housing having a first shell member and a second shell member, a first driving mechanism operable to expand and/or contract the first and second shell members from a first lateral side of the housing, and a second driving mechanism operable to expand and/or contract the first and second shell members from a second lateral side of the housing. The insertion tool includes a chassis, a first measuring mechanism and a second measuring mechanism, a first driving shaft and a first handle. The chassis defines a first channel and a second channel, each extending from a proximal end to a distal end. The first measuring mechanism corresponds to rotation in the first channel and the second measuring mechanism corresponds to rotation in the second channel. The first driving shaft is operable to be inserted into the first channel from the proximal end of the chassis and engage with the first measuring mechanism. The first driving shaft has an end portion configured to engage with the first driving mechanism of the implant device. The first handle is operable to be releasably attached to the first driving shaft for apply torque, thereby allowing the first driving shaft to drive the first driving mechanism of the implant device to effect expansion and/or contraction of the first and second shell members from the first lateral side of the housing of the implant device.

An embodiment of a method includes the steps of providing a spinal interbody fusion system comprising an implant device and an insertion tool, wherein the implant device comprises a housing, a first driving mechanism and a second driving mechanism each being operable to expand and/or contract the housing along a first lateral side and a second lateral side of the housing respectively, and the insertion tool comprises a first driving shaft and a second driving shaft operable to releasably connect with the first and second driving mechanisms of the implant device respectively; connecting the insertion tool with the implant device; inserting the implant device between adjacent vertebrae in a patient; and applying torque to the first and second driving mechanisms of the implant device independently via the first and second driving shaft of the insertion tool, whereby an amount of expansion and/or contraction of the housing along the first lateral side is independently adjusted relative to an amount of expansion and/or contraction of the housing along the second lateral side.

This Summary is provided to introduce selected embodiments in a simplified form and is not intended to identify key features or essential characteristics of the claimed subject matter, nor is it intended to be used as an aid in determining the scope of the claimed subject matter. The selected embodiments are presented merely to provide the reader with a brief summary of certain forms the invention might take and are not intended to limit the scope of the invention. Other aspects and embodiments of the disclosure are described in the section of Detailed Description.

BRIEF DESCRIPTION OF THE DRAWINGS

These and various other features and advantages will become better understood upon reading of the following detailed description in conjunction with the accompanying drawings and the appended claims provided below, where:

DETAILED DESCRIPTION OF EMBODIMENTS

Figure 1:
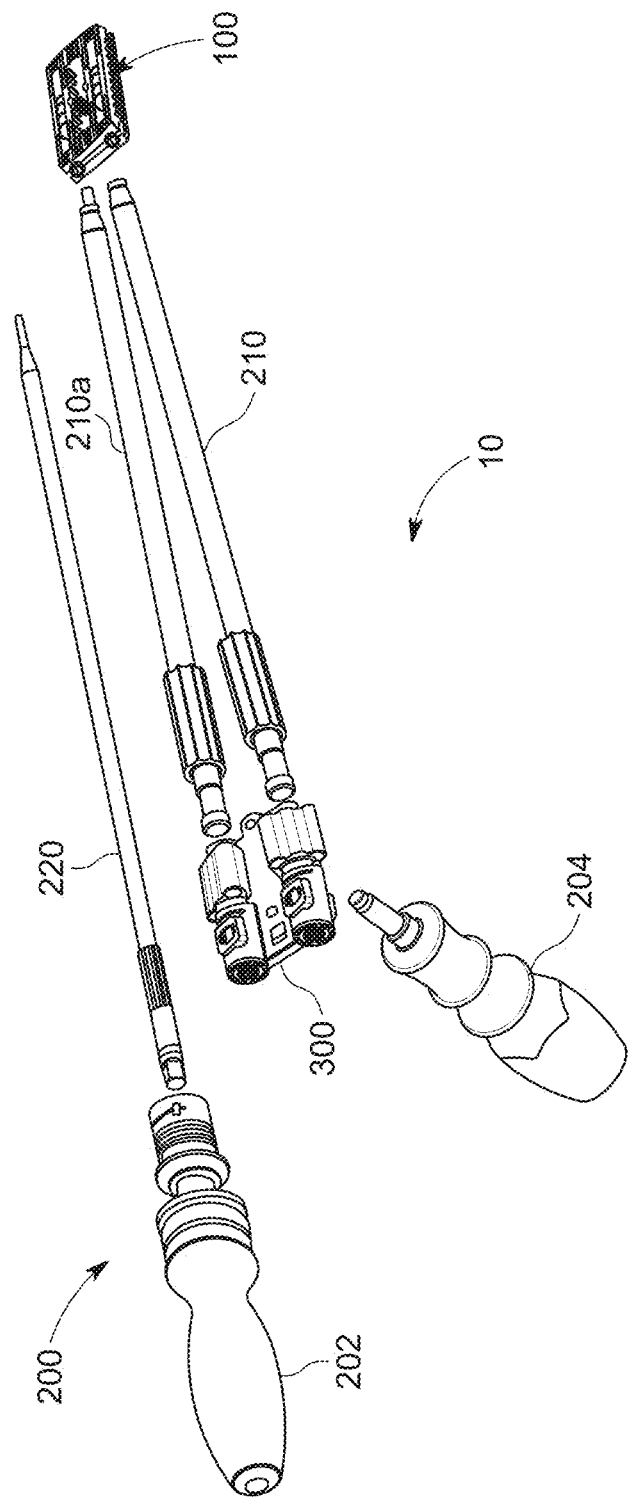
FIG. 1 is an exploded perspective view of an example surgical instrument and an implant device according to embodiments of the disclosure.

Various embodiments of an interbody fusion system, a surgical instrument and method for inserting, removing, and operating a spinal implant device are described.

An example surgical instrument provides a surgeon with dual adjustability in operating an implant device having two distinct rotatable features, allowing the surgeon to apply a 1:1 torque to the implant when positioned in an intervertebral disc space of a patient, simultaneously or independently, to effect an amount of expansion, contraction, or endplate angle adjustment proportionate to the degree of adjustment made to the rotatable features, thereby achieving any possible combination of heights and angles for personalizing the balance or physiological alignment of the patient's spine in an anatomical reference plane such as a sagittal or coronal plane, with a universalized implant device having only a given number of starting heights and lengths (the length measurement being perpendicular to the reference plane). By way of example, in a lateral lumbar interbody fusion (LLIF) procedure, the surgical instrument and implant device can provide anterior and/or posterior adjustment to achieve better sagittal balance or correct sagittal imbalance for the patient. In an anterior lumbar interbody fusion (ALIF) or posterior lumbar interbody fusion (PLIF) procedure, the surgical instrument and implant device can provide lateral and/or contra-lateral adjustment to achieve better coronal balance or correct coronal imbalance for the patient.

An example surgical instrument includes one or two operable torqueing handles for operating an implant device having two distinct rotatable features. When the surgical instrument is used to operate the implant device, the degenerated or collapsed disc space in a patient can be distracted in a unique and efficient way. Distraction can be achieved by operating one of the rotatable features at a time, or by operating both rotatable features in synchrony, which can double the total distraction force, or by using a third option which is that the surgeon works both handles simultaneously but intuitively feels the amount of resistance of each of the rotatable features and turns each one a little more or a little less accordingly. By way of example, if there's more resistance on the first rotatable feature, then the second rotatable feature can be rotated more. The second rotatable feature then shares more of the load and thus frees up the first rotatable feature to rotate and thus expand the implant device more. In contrast to operating an implant device having a single rotatable feature or a device coupling two rotatable features together and driving them from a single handle, the surgical instrument and implant device provided by the present disclosure can replace static instruments needed to distract sequentially and/or other expandable spinal implant technologies that do not distract the intervertebral disc space efficiently.

An example surgical instrument includes a measuring mechanism and scheme. The measuring mechanism and scheme allows a surgeon to receive visual feedback during surgery from two parameters on the instrument related to the extent of restoration added to the implant device on two distinct regions within an anatomical reference plane once implanted into the patient, without the need to count adjustment revolutions during surgery. The two parameters indicated on the instrument can be used to determine other sets of parameters that would be more useful for the surgeon and provided by doing a calculation or consulting a table. By way of example, for sagittal balance restoration, the anterior and posterior indicators of the measuring mechanism and scheme can provide the number of half-turns on each, which can be used to determine anterior height, posterior height and lordosis/kyphosis angle added to the implant. For coronal balance restoration, the lateral and contra-lateral indicators of the measuring mechanism and scheme can provide the number of half-turns on each, which can be used to determine lateral height, contra-lateral height, and coronal correction angle added to the implant.

An example surgical instrument includes a cap assembly. The cap assembly provides a centralized area allowing a surgeon to use impaction force when needed to insert an implant device into an intervertebral disc space in the patient, or use a pull-out force when needed to remove or reposition the implant device within the intervertebral disc space. The cap assembly can be configured to keep both rotatable features of the implant device locked during the attachment and removal of the instrument to and from the implant device. The cap assembly can keep the drivers of the instrument locked until the time when the implant device is adjusted. At the time of adjustment, the cap assembly can be removed. The drivers can be then free to turn for adjustment of the implant device and can be held in place by gravity. The surgeon can readily unsheathe or remove one driver or both drivers from the instrument, and use a single driver in adjusting or driving the first and second rotatable features of the implant device, by unsheathing and re-sheathing of the driver from or to the instrument. When the adjustment of the implant device is completed, the surgeon can optionally return both drivers to place and re-attach the cap assembly to re-secure and lock the drivers to the instrument. The cap assembly can be easily and quickly secured to and released from the instrument by any suitable means including e.g. a push release and a thrust rod mechanism or a lever-release mechanism comprising a torsion spring, as will be described in greater detail below.

An example surgical instrument includes a sleeve-release system for locking and releasing driver sleeves to and from the instrument. The sleeve-release system may include a ball-bearing and spring mechanism, which when in a default lock position, holds the sleeves around the drivers, providing a correction orientation or guidance for the drivers. The ball-bearing and spring mechanism allows the sleeves to rotate freely with little friction and may limit the sleeves to move in an axial direction in a small distance. The ball-bearing and spring mechanism ensures the axis of rotation of the sleeves to be fixed. The free rotation of the sleeves allows the instrument to be connected to the rotatable features of the implant device, which can then be driven by drivers. It should be noted that too much friction on the sleeves would inhibit the expansion process of the implant device. The freedom of the sleeves in axial or in-and-out movement in a small distance allows one sleeve to be fully connected to the implant device before the other sleeve is connected. The axis of rotation of the sleeves can be fixed to ensure a rigid instrument without wobbling, thereby allowing the surgeon to manipulate the position of the implant device within the spinal anatomy. Spinal anatomy is often under a load due to tension in muscles and tendons. Therefore, a strong, solid instrument is desirable to force the working end into place. In addition to the default lock position, the ball-bearing and spring mechanism can have one or more additional positions that allow for assembly or disassembly of the sleeves or possibly other various components of the instrument. The disassembly of sleeves allows more thoroughly cleaning and exposing the instrument to a sterile dose if needed by hospital technical personnel. It also allows the user of the instrument to dis-attach the sleeves to increase direct and fluoroscopic visualization of the implant device once positioned in the patient's body.

With reference to FIGS. 1-17, various embodiments of a surgical instrument and an interbody fusion system will now be described. It should be noted that while some embodiments of the surgical instrument are described in conjunction with placement of an implant device in an intervertebral disc space in the lumbar region of a patient's spine, the surgical instrument can be readily configured for use with an implant device adapted for placement in any other regions of the patient's spine such as the thoracic or cervical region.

Further, it should be noted that the surgical instrument can be used for placement of an implant device using a lateral approach, an anterior approach, a posterior approach, and/or any other approaches or techniques.

Figure 2:
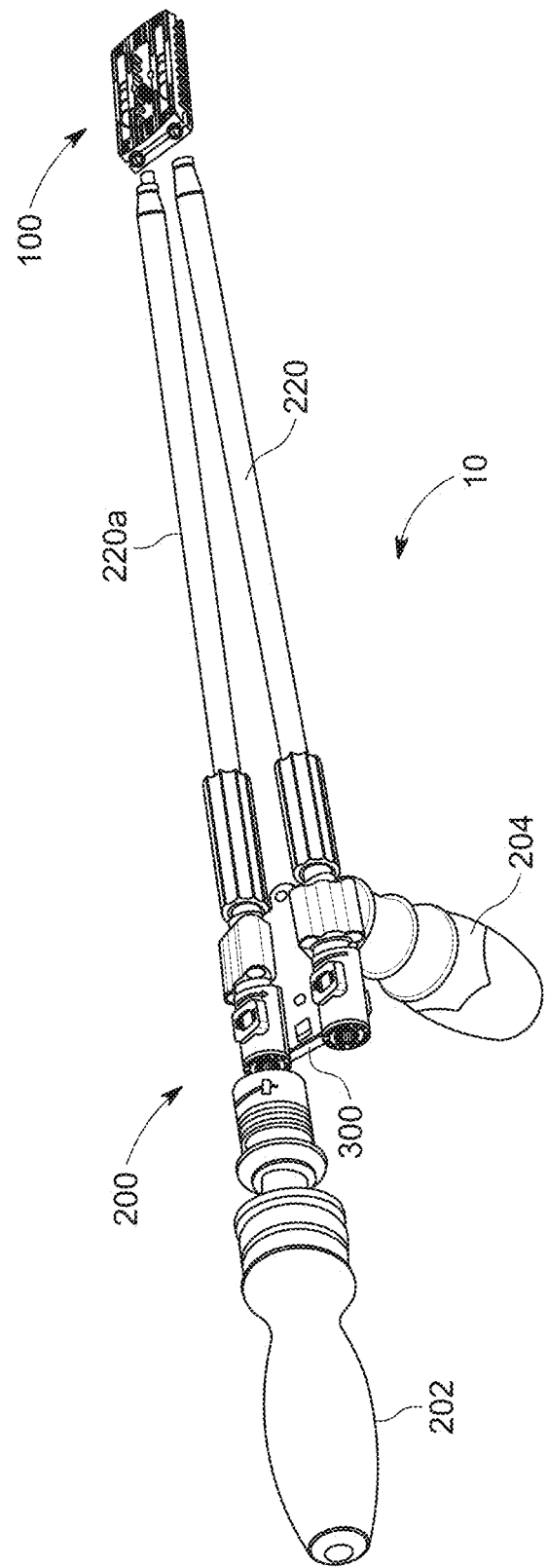
FIG. 2 is an assembled perspective view of the surgical instrument connected with the implant device of FIG. 1 according to embodiments of the disclosure.

FIG. 1 is an exploded view of an example interbody fusion system 10 according to embodiments of the disclosure. FIG. 2 is an assembled view of the interbody fusion system 10 of FIG. 1. As shown, the interbody fusion system 10 comprises an implant device 100 and an insertion tool or surgical instrument 200. The implant device 100 (see also FIG. 6) in general comprises a housing 102, a first rotatable feature or driving mechanism 110 operable to expand and/or contract the housing along a first lateral side 103, and a second rotatable feature or driving mechanism 110a operable to expand and/or contract the housing along a second lateral side 105. The insertion tool or surgical instrument 200 in general comprises a chassis 300, a first tubular sleeve 210 and a second tubular sleeve 210a releasably attached to the chassis 300 respectively, a first driving shaft 220 operable to engage and drive the first and/or second driving mechanisms 110, 110a of the implant device 100 via the first or second tubular sleeve 210, 210a, and a first torqueing handle 202 releasably attached to the first driving shaft 220 for applying torque. The insertion tool 200 may optionally include a guiding handle 204 releasably connected to the chassis 300 for providing a guide for a non-dominant hand of the user in operating the instrument 200.

Figure 3:
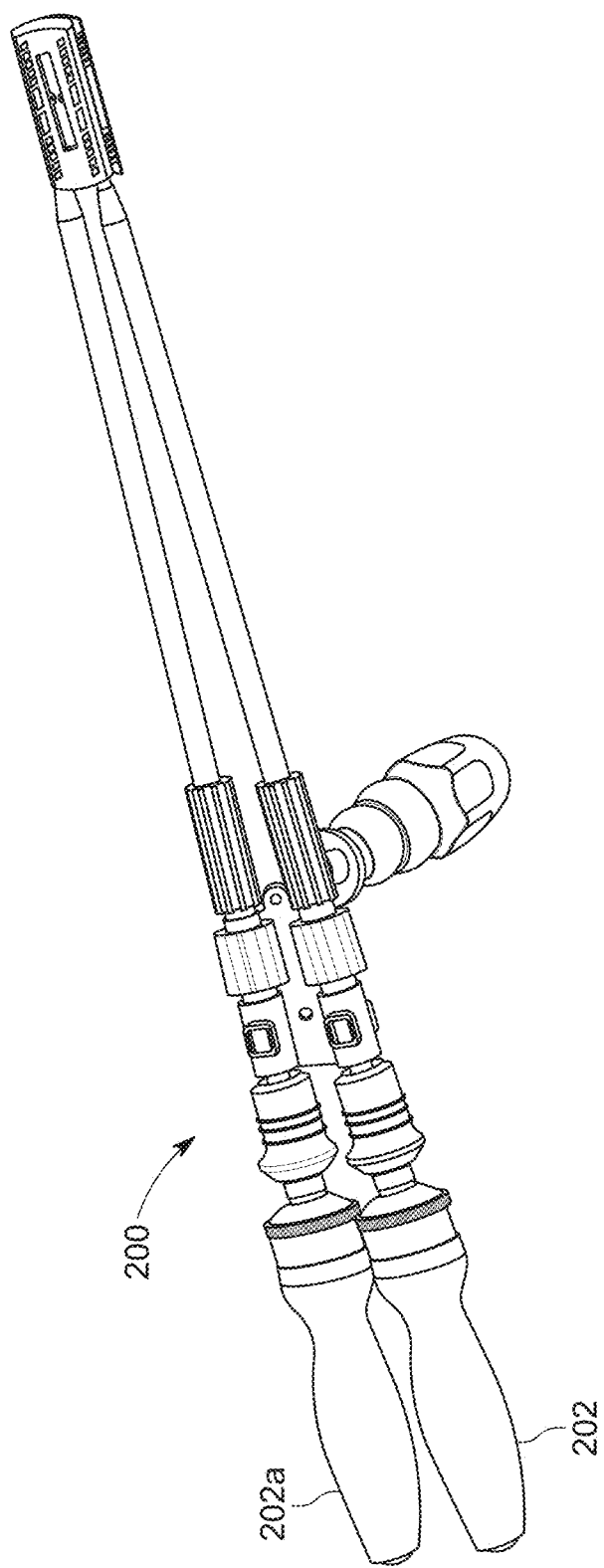
FIG. 3 is a perspective view of an example interbody fusion system according to embodiments of the disclosure.
Figure 4:
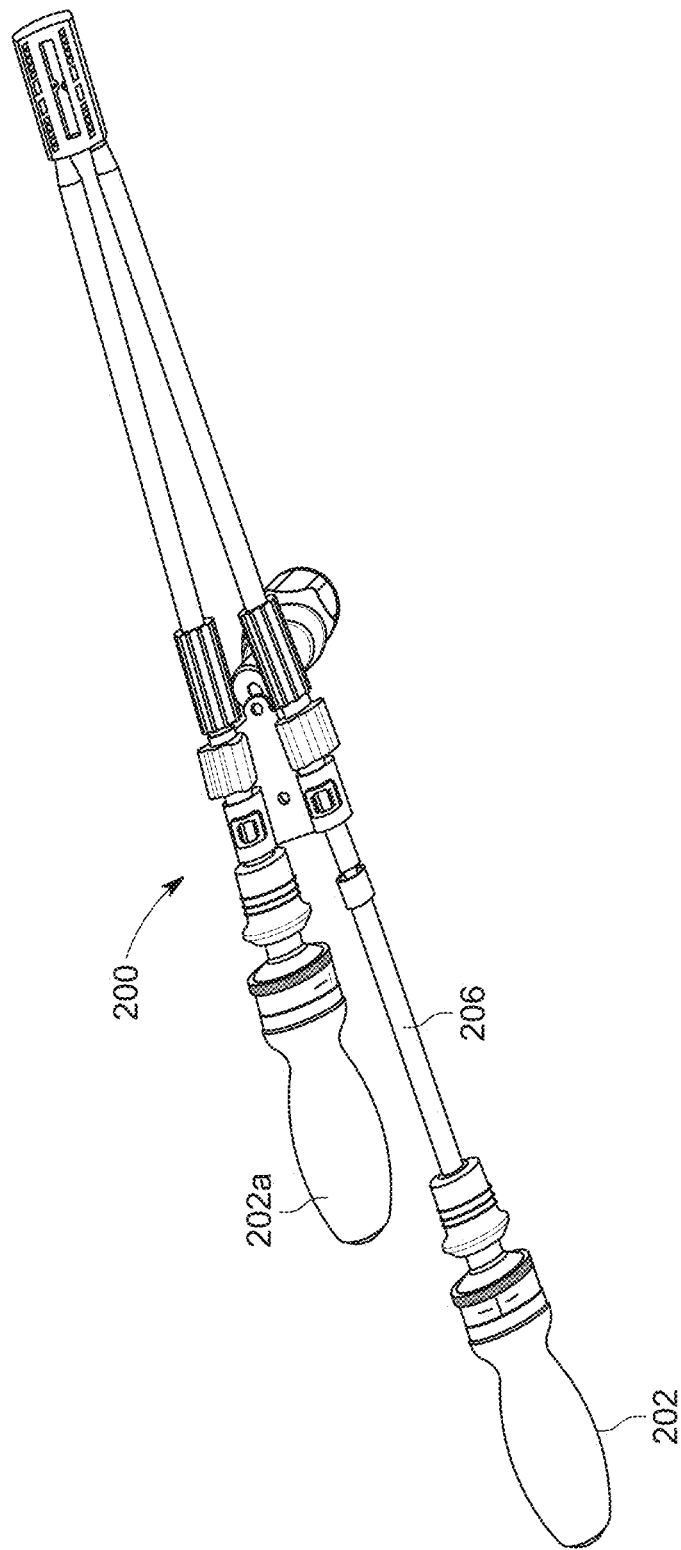
FIG. 4 is a perspective view of an example interbody fusion system according to embodiments of the disclosure.
Figure 5:
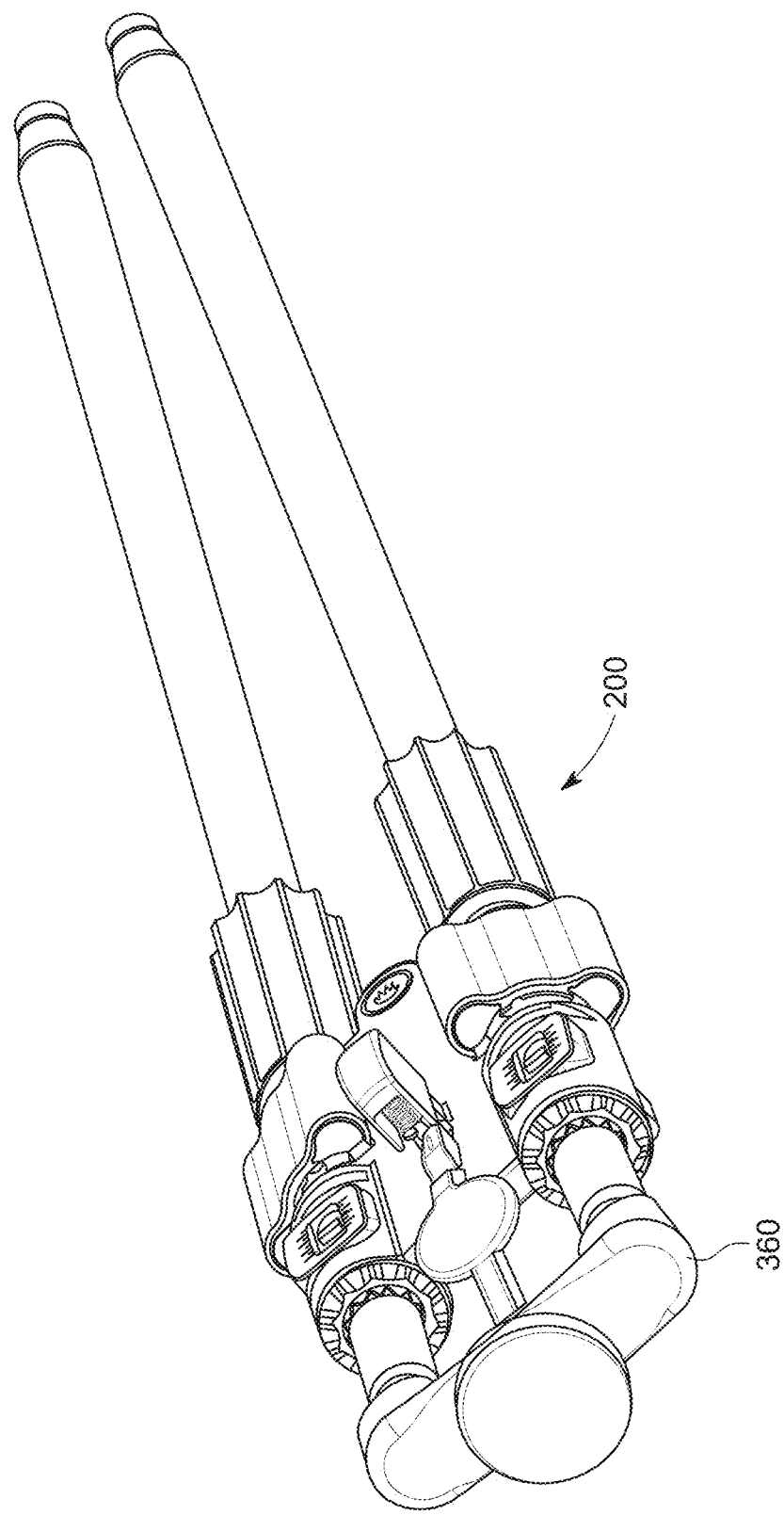
FIG. 5 is a perspective view of an example interbody fusion system according to embodiments of the disclosure.

The surgical instrument or insertion tool 200 may optionally include two driving shafts and two torqueing handles, a first torqueing handle being releasably attached to a first driving shaft and a second torqueing handle being releasably attached to a second torqueing shaft. Two driving shafts and two torqueing handles allow independent operation of both driving mechanisms of the implant device, simultaneously or alternatively, providing the surgeon with more flexibility and control in expansion, contraction, and/or adjustment of the implant device, to be described in greater detail below. FIG. 3 shows an example surgical instrument 200 comprising two torqueing handles 202, 202a and two driving shafts (not shown in FIG. 3). The surgical instrument 200 may optionally include an adapter which can be readily coupled to one of the driving shafts. The adapter allows offset of the torqueing handles, providing the surgeon with more ease of gripping. FIG. 4 shows an example surgical instrument 200 comprising two torqueing handles 202, 202a and an adapter 206. The surgical instrument 200 may include a cap assembly which can be releasably attached to the instrument, providing a centralized area for receiving an impaction or pull-out force or performing other functions of the instrument, to be described in greater detail below. FIG. 5 shows an example surgical instrument 200 comprising a cap assembly 360.

Figure 6:
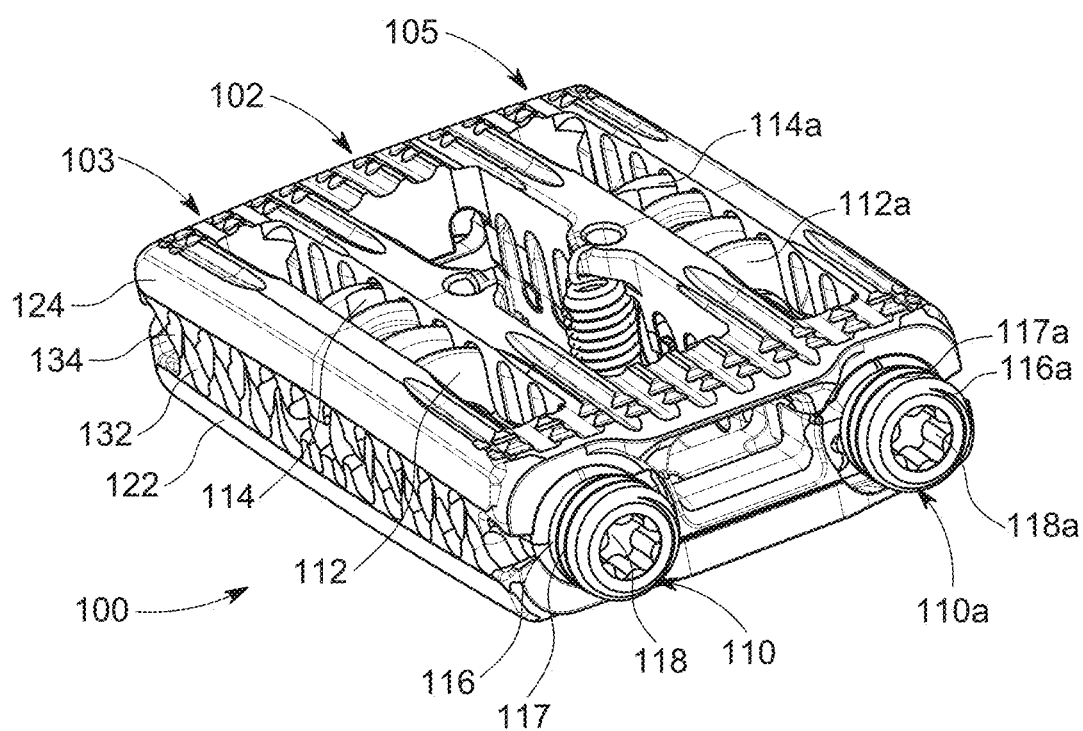
FIG. 6 is a perspective view of an example implant device according to embodiments of the disclosure.
Figure 7:
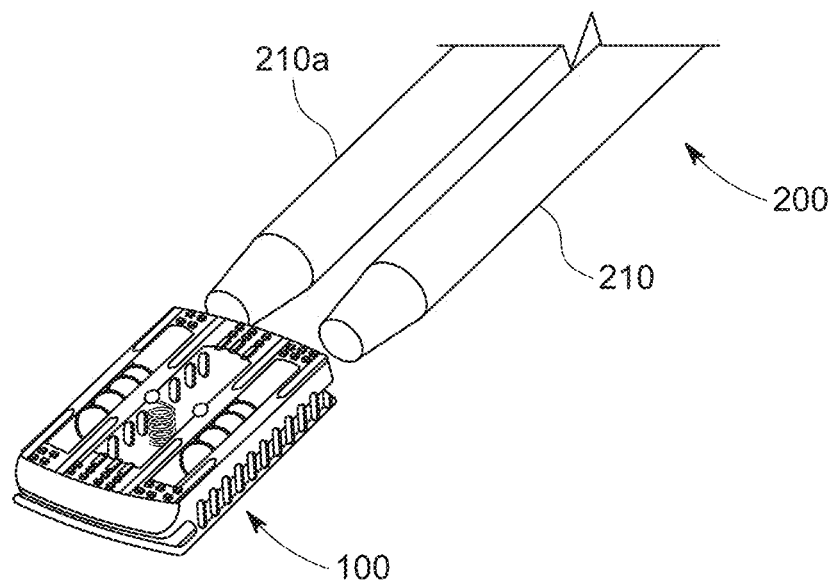
FIG. 7 is a perspective view illustrating connection of an insertion tool with an implant device according to embodiments of the disclosure.
Figure 8A:
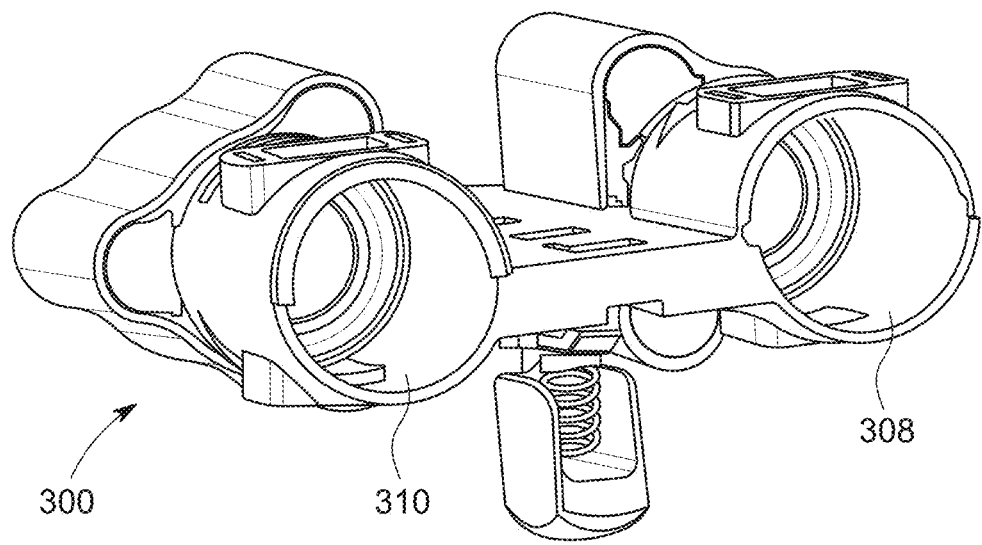
FIG. 8A is a top perspective view of an example chassis according to embodiments of the disclosure.
Figure 8B:
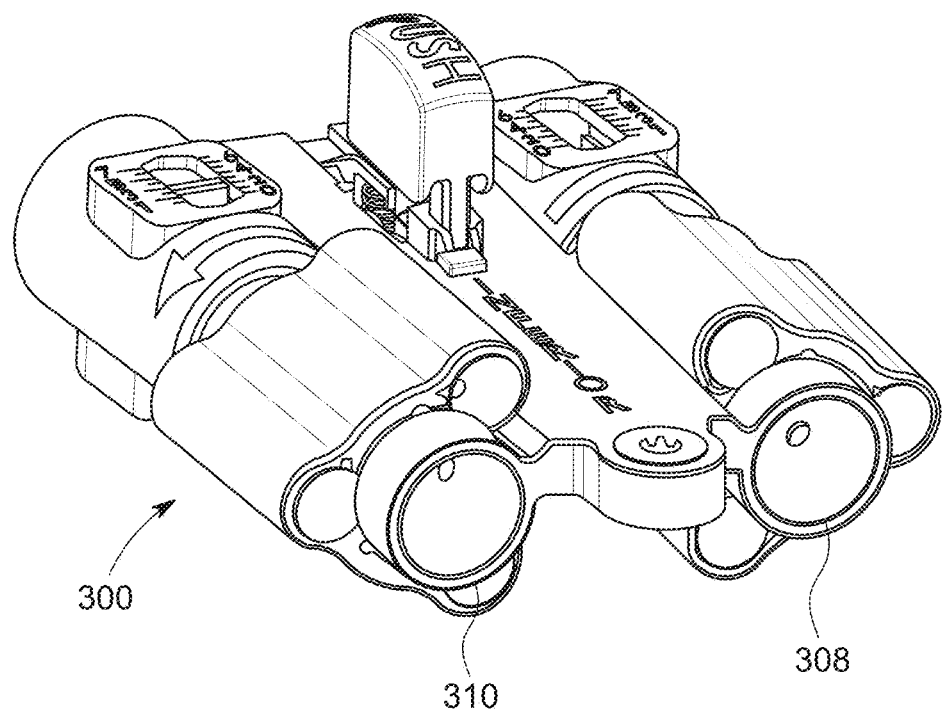
FIG. 8B is a bottom perspective view of the chassis of FIG. 8A.
Figure 8C:
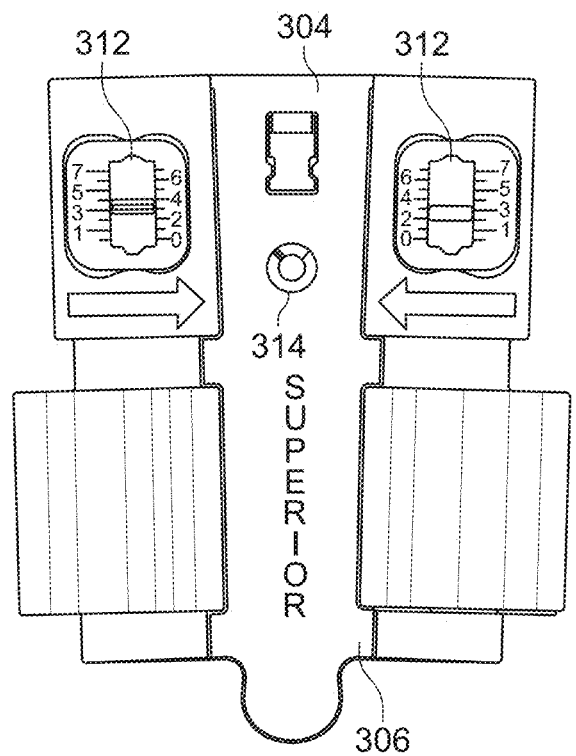
FIGS. 8C and 8D are side views of the chassis of FIG. 8A.
Figure 8D:
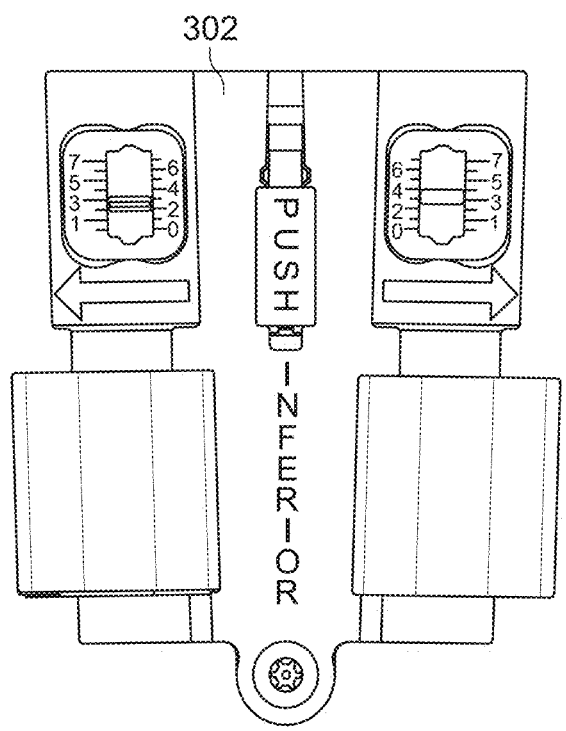

With reference to FIG. 6, the example implant device 100 includes an expandable housing 102, a first driving mechanism 110 and second driving mechanism 110a. The first driving mechanism 110 may include a first pair of cam members 112, 114 and a first shaft 116 engaging with the first pair of cam members 112, 114. The second driving mechanism 110a may include a second pair of cam members 112a, 114a and a second shaft 116a engaging with the second pair of cam members 112a, 114a. Each of the first and second shafts 116, 116a may include features at their end portions for connecting with the insertion tool or surgical instrument 200 and for receiving and engaging a driving shaft of the surgical instrument. By way of example, the first and second shafts 116, 116a may have male features 117, 117a for connection with the tubular sleeves 210, 210a of the insertion tool 200 and female features 118, 118a for receiving and engaging a driving shaft 220 of the insertion tool. Other suitable configurations or features can be used for connecting and engaging the insertion tool and the claims of this disclosure are not so limited. FIG. 7 illustrates an example of connecting an insertion tool 200 with an implant device 100, by using internal threads provided at the end portions of the tubular sleeves 210, 201a of the insertion tool 200 and the external threads at the end portions of the first and second driving mechanisms 110, 110a of the implant device 100. It should be noted that other suitable connection means can be used and the claims of the disclosure are not so limited.

The housing 102 includes a first or bottom shell member 122 and a second or top shell member 124. The bottom shell member 122 may include a plurality of individual riser members 132. The top shell member 124 may include a plurality of individual riser members 134. The plurality of individual riser members 132, 134 of the bottom and top shell members 122, 124 may define a first step tracking run along a first lateral side 103 of the housing 102 and a second step tracking run along a second lateral side 105 of the housing 102. The height of the plurality of individual riser members 132, 134 may change along the first and second step tracking runs. For example, the height of the plurality of individual riser members 132, 134 of each of the first and second step tracking runs may increase from a central portion of the step tracking extending distally from the central portion. The first and second pairs of cam members 112, 114, 112a, 114a may each comprise an external helical thread having a thickness configured to fit in the gaps between adjacent individual riser members 132, 134.

The first shaft 116 is operable to rotate the first pair of cam members 112, 114, causing the first pairs of cam members 112, 114 to move on the individual riser members 132, 134 defining the first step tracking run. The second shaft 116a is operable to rotate the second pair of cam members 112a, 114a, causing the second pair of cam members 112a, 114a to move on the individual riser members 132, 134 defining the second step tracking run. In response to the rotation of the first and second pairs of cam members 112, 114, 112a, 114a, the bottom and top shell members 122, 124 may move relative to each other, effecting an expansion of the housing or a contraction of the housing from the expansion by reversing the rotation of the first and/or second pairs of cam members. The first and second shafts 116, 116a may be operable independently of each other. Therefore, the degree of expansion or contraction of the first lateral side 103 of the housing 102 is independently adjustable relative to the degree of expansion or contraction of the second lateral side 105 of the housing 102 when the first and second sets of cam members 112, 114, 112a, 114a are rotated independently to different positions on the first and second step tracking runs.

The positions of the plurality of individual riser members 132 on the bottom shell member 122 may arrange to offset from the positions of the plurality of individual riser members 134 on the top shell member 124 so that the plurality of individual riser members 132 of the bottom shell member 122 may intermesh the plurality of individual riser members 134 of the top shell member 124 when the housing 102 is in a contraction configuration.

Various embodiments of an implant device are described in U.S. Pat. Nos. 9,889,019 and 10,188,527, and U.S. Ser. No. 16/569,621 filed Sep. 12, 2019 entitled "Expandable and Adjustable Lordosis Interbody Fusion System." The disclosures of U.S. Pat. Nos. 9,889,019 and 10,188,527, and U.S. Ser. No. 16/569,621 are herein incorporated by reference in their entirety. Further, it should be noted that the example implant device 100 is described herein for illustration purpose. The surgical instrument 200 of the disclosure can be used or readily adapted or modified to operate any other suitable implant devices having two rotatable features.

With reference to FIGS. 8A-8D and FIGS. 1-2, the surgical instrument 200 comprises a chassis 300. The chassis 300 provide a main support and an assembly point of the surgical instrument 200. The chassis 300 may be constructed from a metal such as stainless steel or a medical grade plastic providing for a rugged operating instrument. As shown, the chassis 300 comprises a body 302 having a proximal end 304 and a distal end 306, a first hollow channel 308 extending between the proximal end 304 and the distal end 306, and a second hollow channel 310 extending between the proximal end 304 and the distal end 306. The first and second channels 308, 310 may be sized and shaped to provide two independent passageways for a driving shaft 220 to be inserted through.

The first and second channels 308, 310 may be spaced apart. The distance between the first and second channels 308, 310 may depend on the size and/or shape of the implant device 100 to be operated with the surgical instrument 200. Depending on the size and/or shape of the implant device, and the length of the driving shafts and sleeves, the first and second channels 308, 310 may be configured to be substantially parallel or slightly leaning to each other towards their distal ends, forming a small angle. The slightly angled configuration may provide more space at the proximal end of the chassis for operating the instrument provided with two torqueing handles.

In some embodiments, at the proximal end portion 304 of the chassis 300, the first channel 308 may be sized, shaped, or configured to accommodate or house a first measuring mechanism, and the second channel 310 may be sized, shaped, or configured to accommodate or house a second measuring mechanism. Windows 312 and marking schemes 314 near the windows may be provided to indicate and/or quantify measurements provided by the measuring mechanisms. The measuring mechanisms and schemes will be described in greater detail below. At the distal end portion 306 of the chassis 300, the first and second channels 308, 310 may be sized to allow a portion of the first and second tubular sleeve 210, 210a to slide into, which can be secured and released by a first and a second sleeve-release mechanisms respectively. The sleeve-release mechanisms will be described in greater detail below.

On the outer surface of the chassis body, various markings, indicia or user interface may be provided. For example, indicia "INFERIOR" and "SUPERIOR" may be provided on the body surface to help simplify the directional orientation of the instrument during use. In some embodiments, the chassis body may be provided with features 314 such as a threaded hole to connect a handle for guiding a non-dominant hand of a user in operating the surgical instrument.

With reference to FIGS. 9A-9B and FIGS. 1-2, the surgical instrument 200 may include a measuring system 320. The measuring system 320 serves to provide a surgeon with visual feedback about the extent of restoration added to the implant device during surgery, or about revolutions of the driving shafts in operating the implant device. The measuring system 320 may be configured to provide two independent or separate parameters on the instrument, thereby providing the surgeon with visual feedback about restoration added to the implant device on two distinct regions within an anatomical reference plane during surgery. By way of example, the measuring system 320 may include a first measuring system 322 configured to provide parameters on the instrument about the extent of expansion, contraction, or adjustment of the first lateral side of the implant device, and a second measuring system 322a configured to provide parameters on the instrument about the extent of expansion, contraction, or adjustment of the second lateral side of the implant device.

Figure 9A:
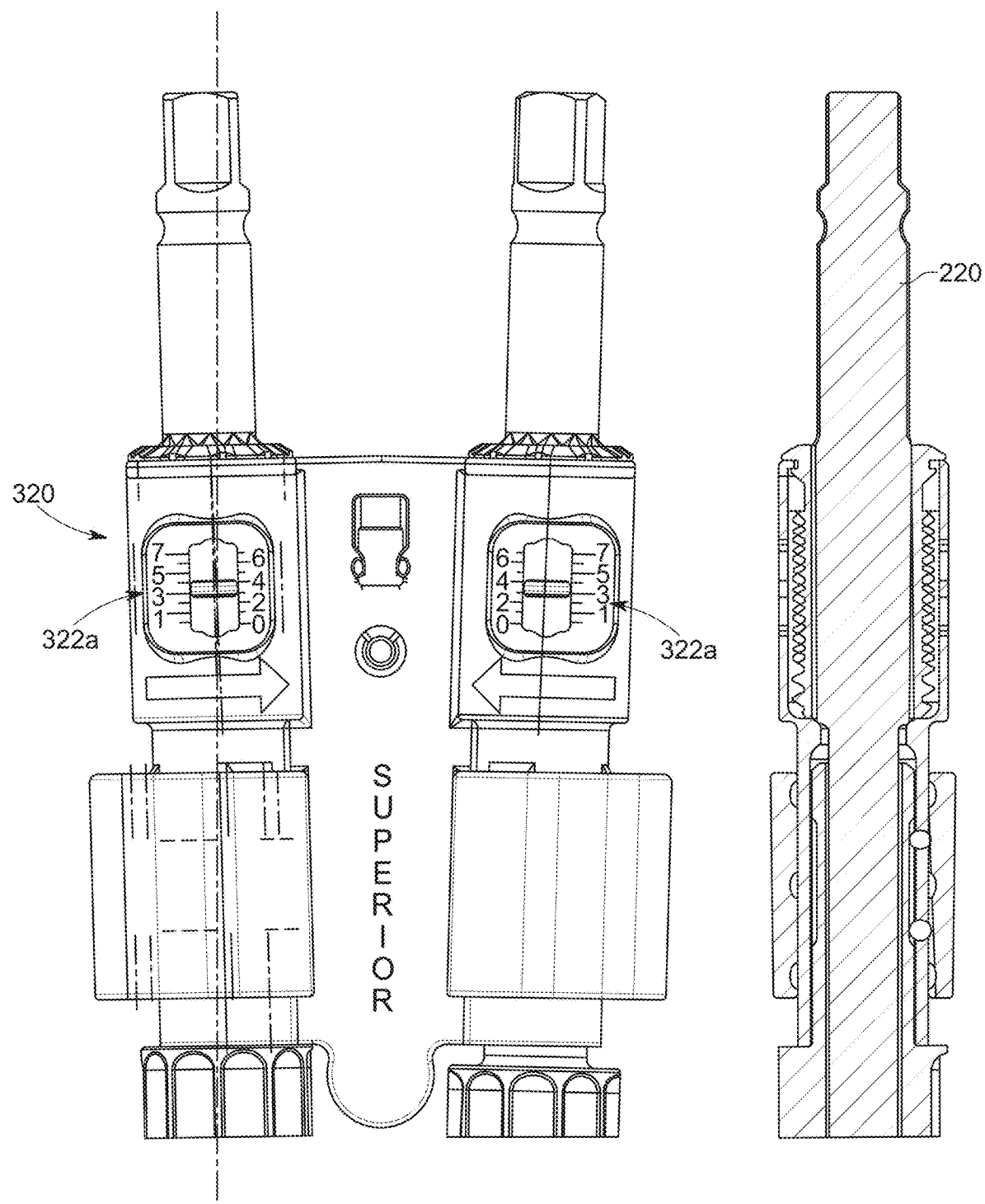
FIG. 9A shows a cross-sectional view of a measuring system according to embodiments of the disclosure.
Figure 9B:
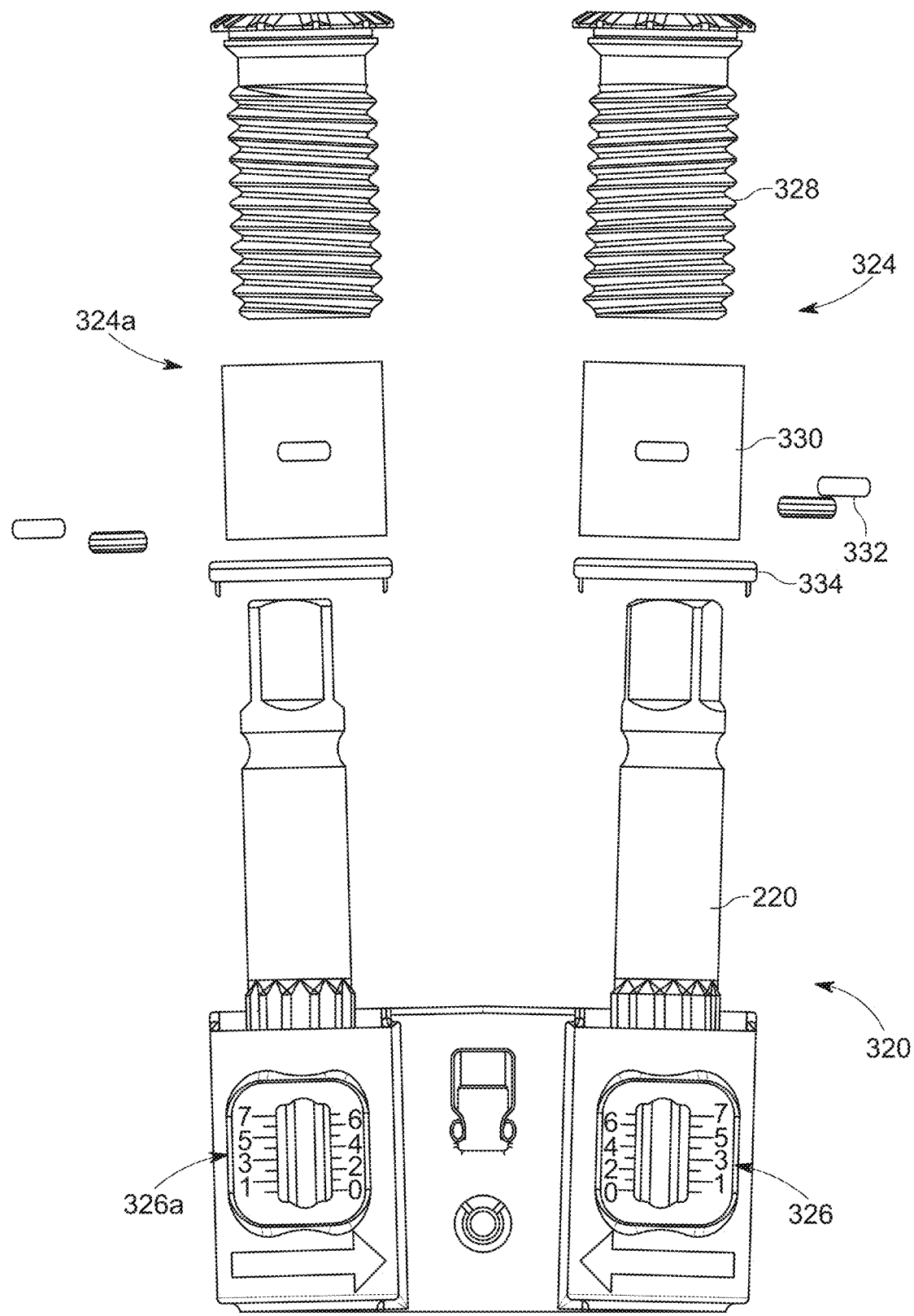
FIG. 9B shows an exploded view of the measuring system of FIG. 9A.

As shown in FIGS. 9A-9B, an example first measuring system 322 may include a first measuring mechanism 324 and a first measuring scheme 326. The first measuring mechanism 324 may include a first indicator adapter 328, a first indicator cylinder 330, and first indicator pins 332. The first measuring scheme 326 may include indicator markings on the chassis adjacent to the windows in the proximal end portion of the chassis. The internal surface of the first indicator adapter 328 may be provided with features such as teeth, grooves or the like configured to engage with features such as external teeth, grooves or the like on the first driving shaft 220. The internal surface of the first indicator cylinder 330 may be provided with threads to engage with external threads on the first indicator adapter 328. The first indicator pins 332 may be fixed on the first indicator cylinder 330 and protrude out of the windows when assembled. The first indicator adapter 328 and first indicator cylinder 330 may be retained in the chassis 300 by a first retainer 334 when assembled. In operation, the rotation of the first driving shaft 220 causes a rotational movement of the first indicator adaptor 328, which in turn transfers the rotational movement to the first indicator cylinder 330. The first indicator cylinder 330 receives the rotational movement from the first indicator adaptor 328 and converts the rotational movement into linear motion, moving the indicator pins 332 up and down. The indicator pins 332 align with the marking scheme 326 on the chassis, providing the surgeon with a measured configuration of the implant device added by the operation of the first driving shaft 320 from the first lateral side of the implant device. The first indicator pins 332 may also serve to prevent the user from over-expanding or over-contracting the implant device during operation. Once the first indicator pins 332 reach the top or bottom of their track on the chassis, further adjustment of the implant device would be prohibited. This helps to further ensure that the implant device is used properly during surgery.

As shown in FIG. 9A-9B, an example second measuring system 322a may include a second measuring mechanism 324a and a second measuring scheme 326a. The construction and operational principle of the second measuring mechanism and scheme 324a, 326a are similar to those of the first measuring mechanism and scheme 324, 326, and therefore, their detailed description is omitted herein to avoid obscuring description of the disclosure.

The first and second measuring schemes 326, 326a may be configured to provide visual indication about the height of the implant device inserted at the intervertebral disc space. By way of example, one marking unit on the measuring scheme may correspond to e.g. a half-turn of the driving shaft, which may in turn correspond to e.g. 1.1 mm height of the implant device. The difference of the parameters on the first and second measuring schemes can be used to determine the spinal balance such as lordosis, kyphosis, or coronal offset etc. By way of example, a difference in one marking unit between the first and second measuring schemes 326, 326a may indicate e.g. about 4.8 degrees of lordosis/kyphosis. Further, the parameters shown on the instrument can be used to determine other sets of parameters that would be more useful for a surgeon and would be provided by doing a calculation or consulting a table. The first measuring scheme 326 may include a starting position and a maximum position, and the linear measurement of the first measuring scheme 326 may correspond to the cumulative rotations of the driving shaft while adjusting an adjustable feature on the implant device. Similarly, the second measuring scheme 326a may include a starting position and a maximum position, and the linear measurement of the second measuring scheme may correspond to the cumulative rotations of the driving shaft while adjusting an adjustable feature on the implant device.

Therefore, the measuring system 320 of this disclosure allows a surgeon to receive visual feedback from two independent parameters on the surgical instrument during surgery about the restoration added to the spinal implant on two distinct regions without the need to count drive revolutions during surgery. For sagittal balance restoration, the first and second measuring schemes can be configured to indicate the anterior height and posterior height respectively, and the difference in heights may be used to determine the lordosis/kyphosis angle added to the implant. For coronal balance restoration, the first and second measuring schemes may be configured to indicate lateral height and contralateral height respectively and the difference in heights may be used to determine the coronal correction angle added to the implant.

With reference to FIGS. 10A-10C and FIGS. 1-2, the surgical instrument 200 may include a cap assembly 340. The cap assembly 340 is operable to be releasably attached to the chassis 300 and configured to prevent the first and second driving shafts 220, 220a from rotating when the cap assembly 340 is attached, thereby keeping the first and second rotating mechanisms of the implant device 100 locked during the attachment or removal of the instrument 200 to or from the implant device 100. The cap assembly 340 may be adapted to receive an impaction force in a forward direction if needed to insert the implant device 100 into the intervertebral disc space, and/or be adapted to receive a pull-out force applied e.g. by a slap hammer if needed to remove or reposition the implant device 100 within the intervertebral disc space.

Figure 10A:
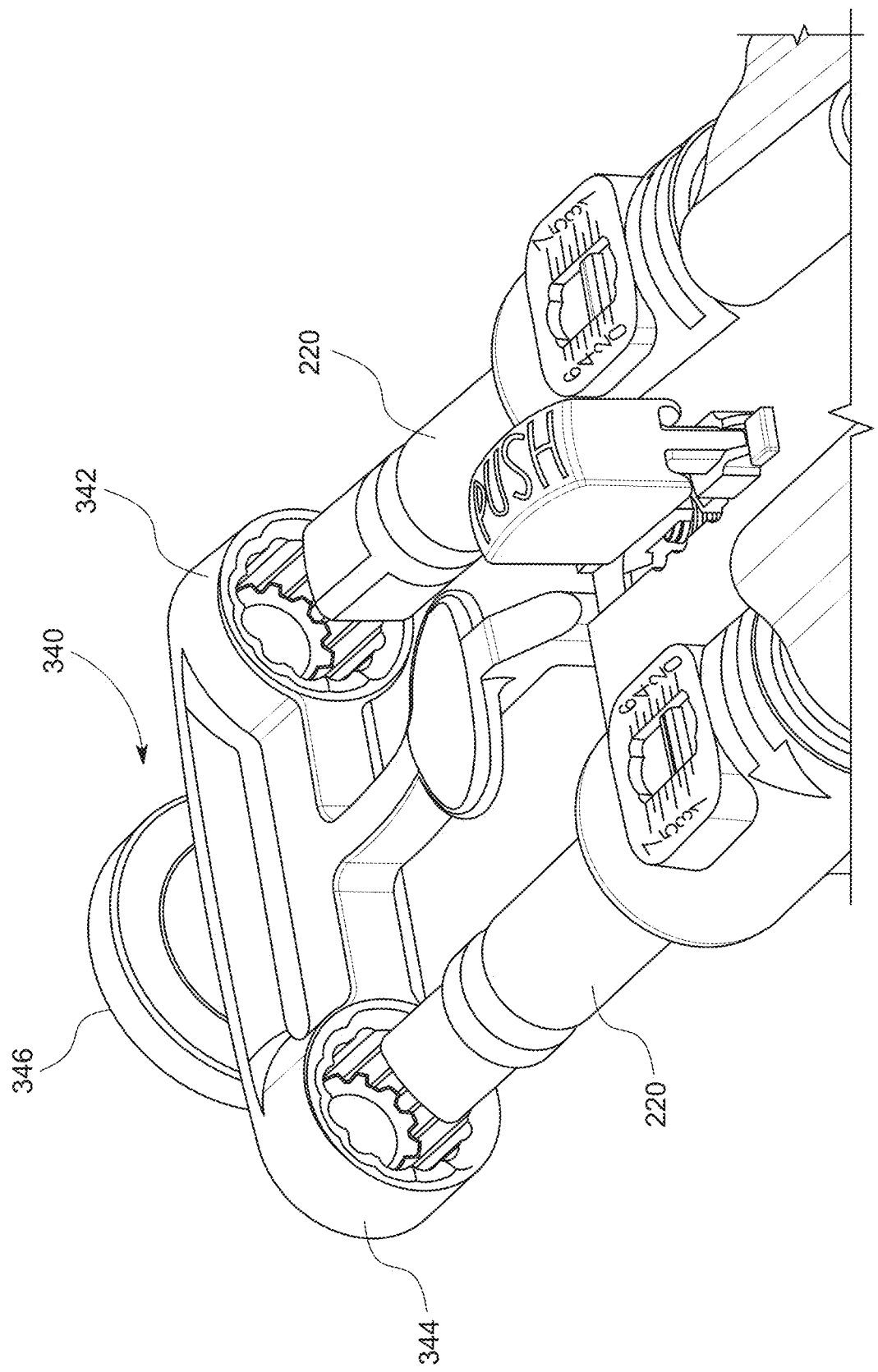
FIG. 10A depicts an example cap assembly according to embodiments of the disclosure.
Figure 10C:
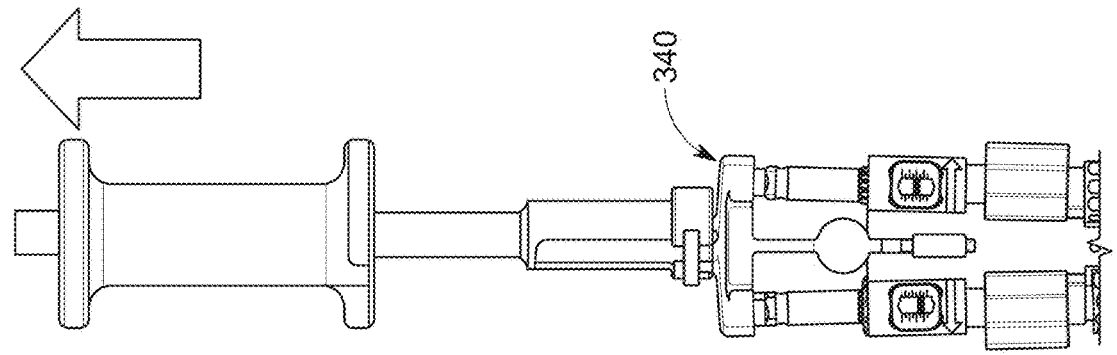
FIG. 10C depicts another application of the cap assembly of FIG. 10A.
Figure 10B:
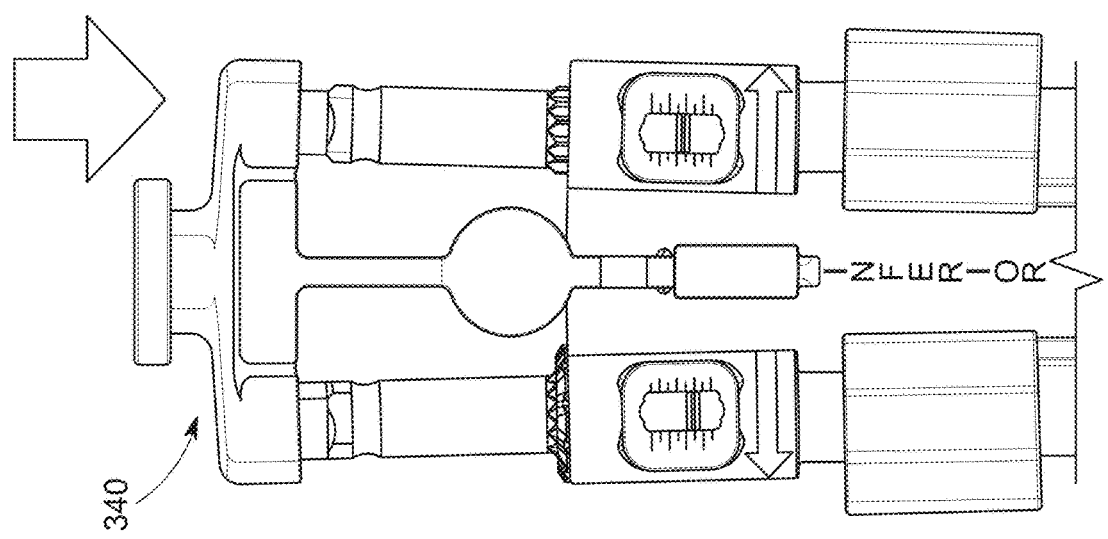
FIG. 10B depicts an application of the cap assembly of FIG. 10A.

FIG. 10A shows an example cap assembly 340 comprising a first cap 342 and a second cap 344. The first and second caps 342, 344 are configured to couple with the first and second driving shafts 220, 220a respectively when the torqueing handles are removed. The first and second caps 342, 342a may include ribbed female features configured to fit over the male features on the first and second driving shafts 220, 220a to prohibit rotation of the first and second driving shafts when the cap assembly is attached (FIG. 10A). The example cap assembly 340 may further comprise a third cap 346 configured to receive an impaction force (FIG. 10B). The cap assembly 340 may be constructed from a metal such as stainless steel to allow the user to deliver an impaction force with e.g. a mallet and transfer a force down to the implant device to aid insertion of the implant device into the intervertebral disc space. The third cap 346 may have a geometry e.g. a circular disc with a neck, or any other suitable geometry to serve as a gripping point or site for connecting with a slap hammer to receive a pull-out force to remove the implant device out of or reposition the implant device in the intervertebral disc space (FIG. 10C).

Figure 11A:
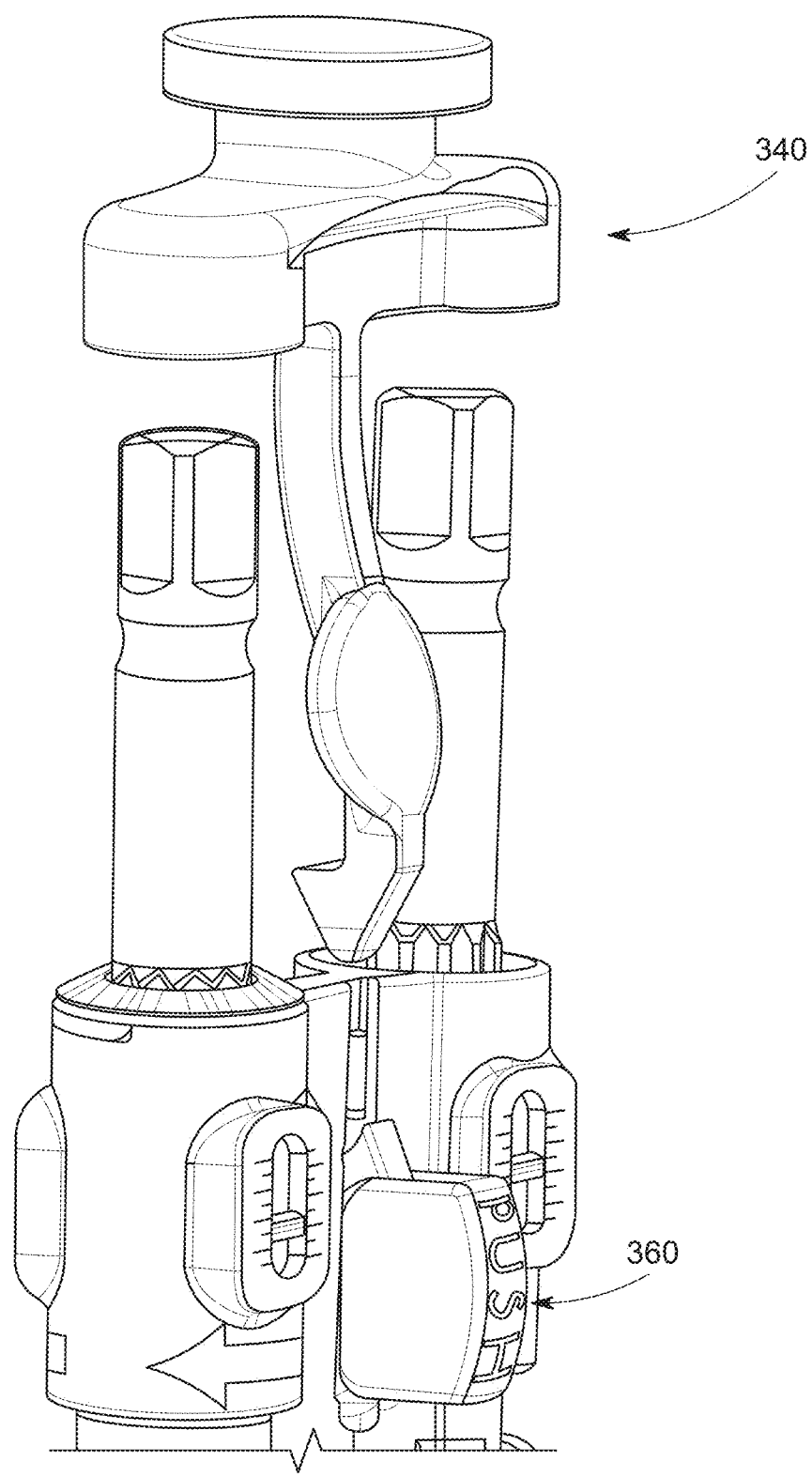
FIG. 11A depicts an ejector release mechanism and an example cap assembly according to embodiments of the disclosure.
Figure 11C:
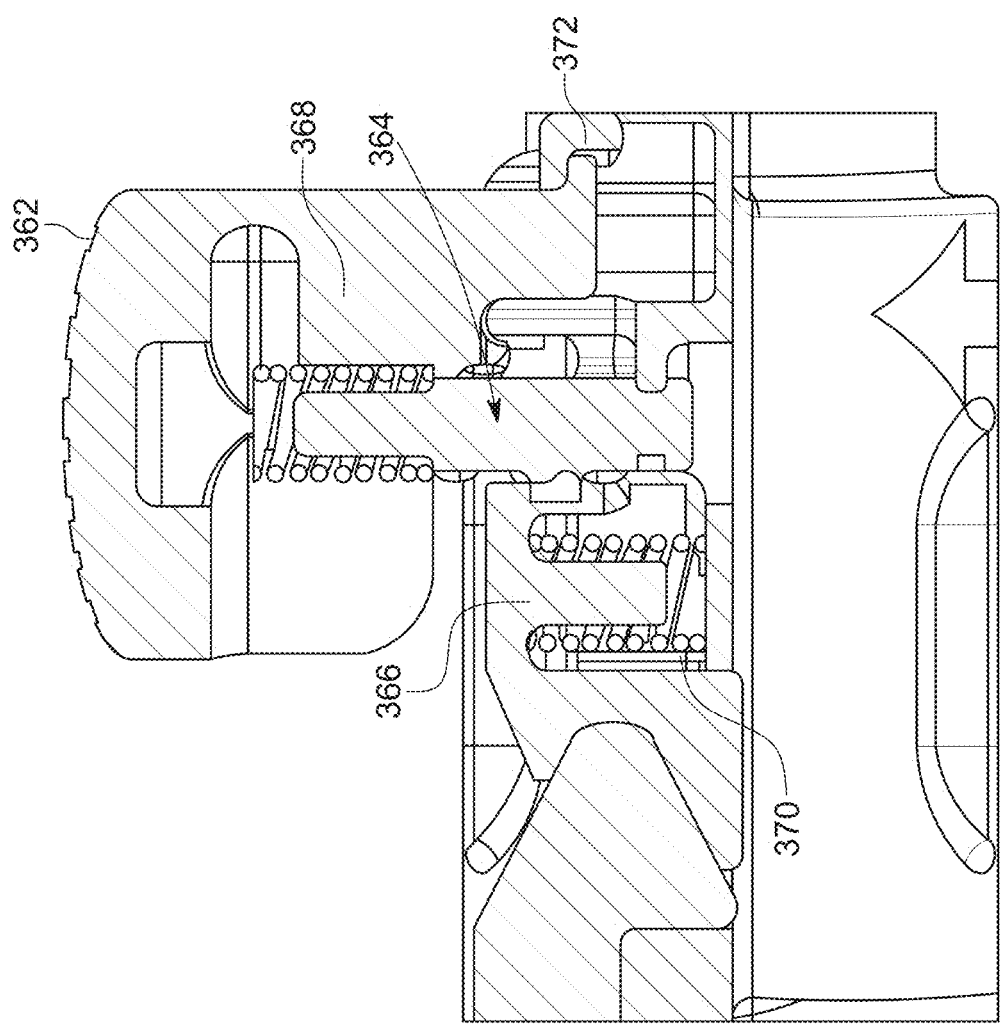
FIG. 11C is shows a cross-sectional view of the ejector release mechanism of FIG. 11B.
Figure 11B:
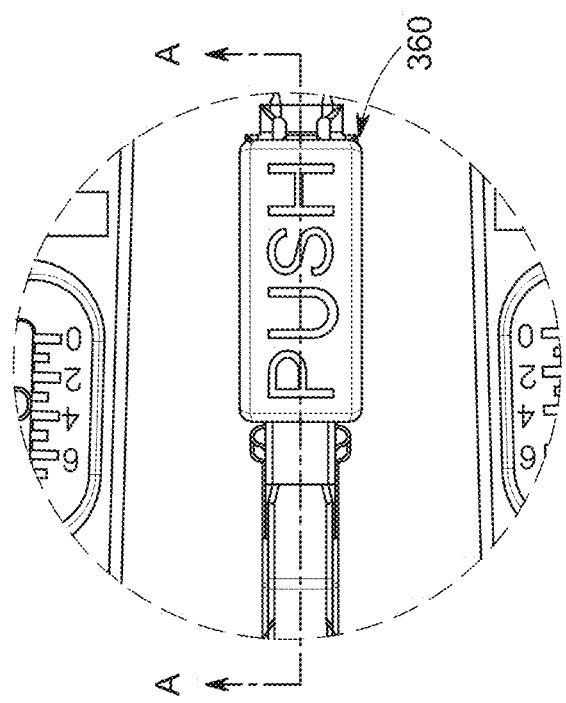
FIG. 11B shows a top view of the ejector release mechanism of FIG. 11A.

With reference to FIGS. 11A-11C, the cap assembly 340 may be attached to and released from the instrument by a cap ejector mechanism 360. As shown, the example ejector mechanism 360 includes an ejector button 362, an ejector rod 364, ejector 366, compression springs 368, 370 held on the ejector rod 364 and ejector 366, and a button retainer 372 to secure the push button to the chassis and keep it in place. In operation, when the push button 362 is pushed inwardly for example, the compression spring 368 on the ejector rod 364 is forced from a free state to a compressed state. The push button 362 then interferes with the ejector rod 364, forcing the ejector rod 364 to rotate. Upon rotating, the ejector rod 364 contacts or interferes with the ejector 366, allowing the compression spring 370 on the ejector 366 to move outwardly from a compressed state to a free state. The tail of the cap assembly 340 is then free to be pulled out by the user. Other suitable push release and thrust rod mechanisms can also be used to attach and release the cap assembly.

Figure 11D:
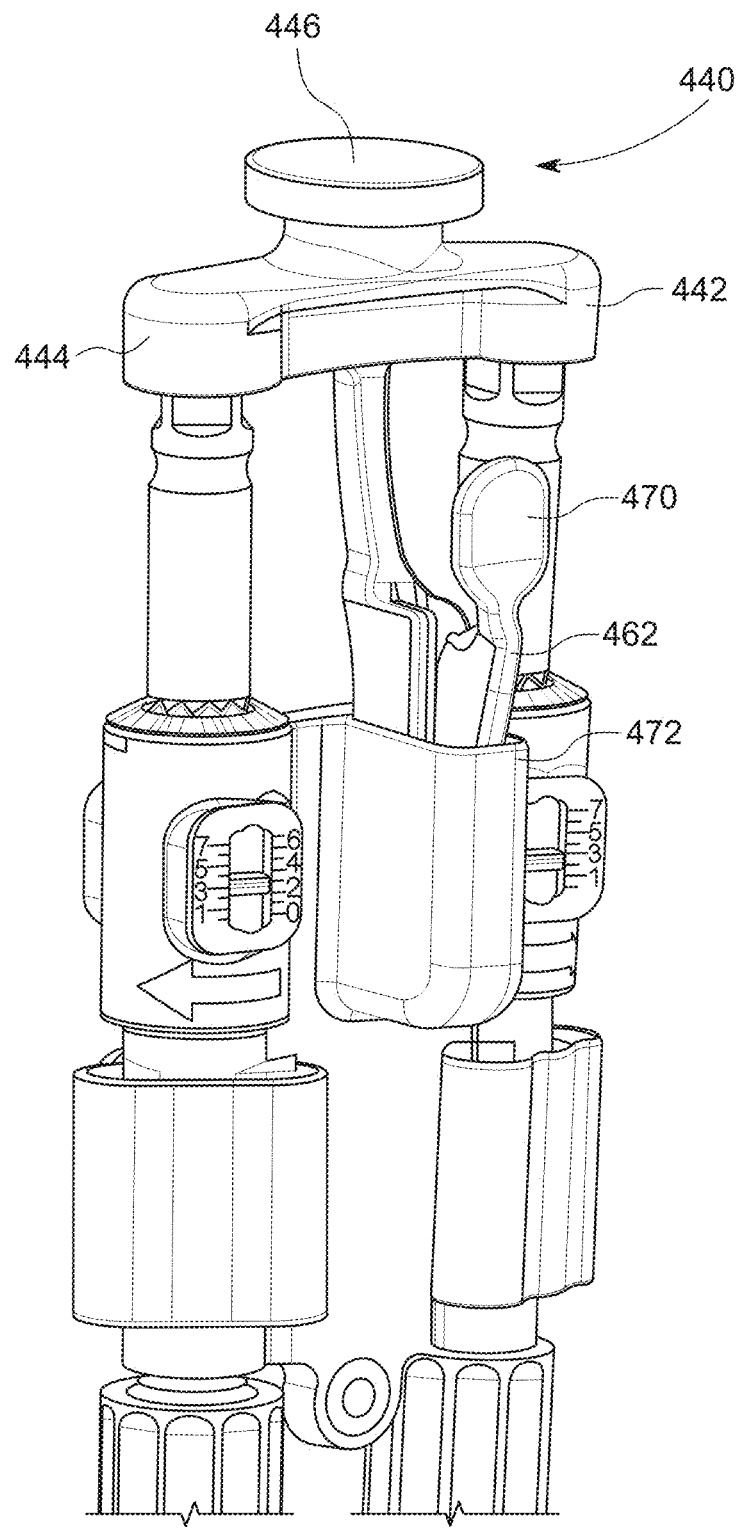
FIGS. 11D-11F depict an example cap assembly according to embodiments of the disclosure.
Figure 11E:
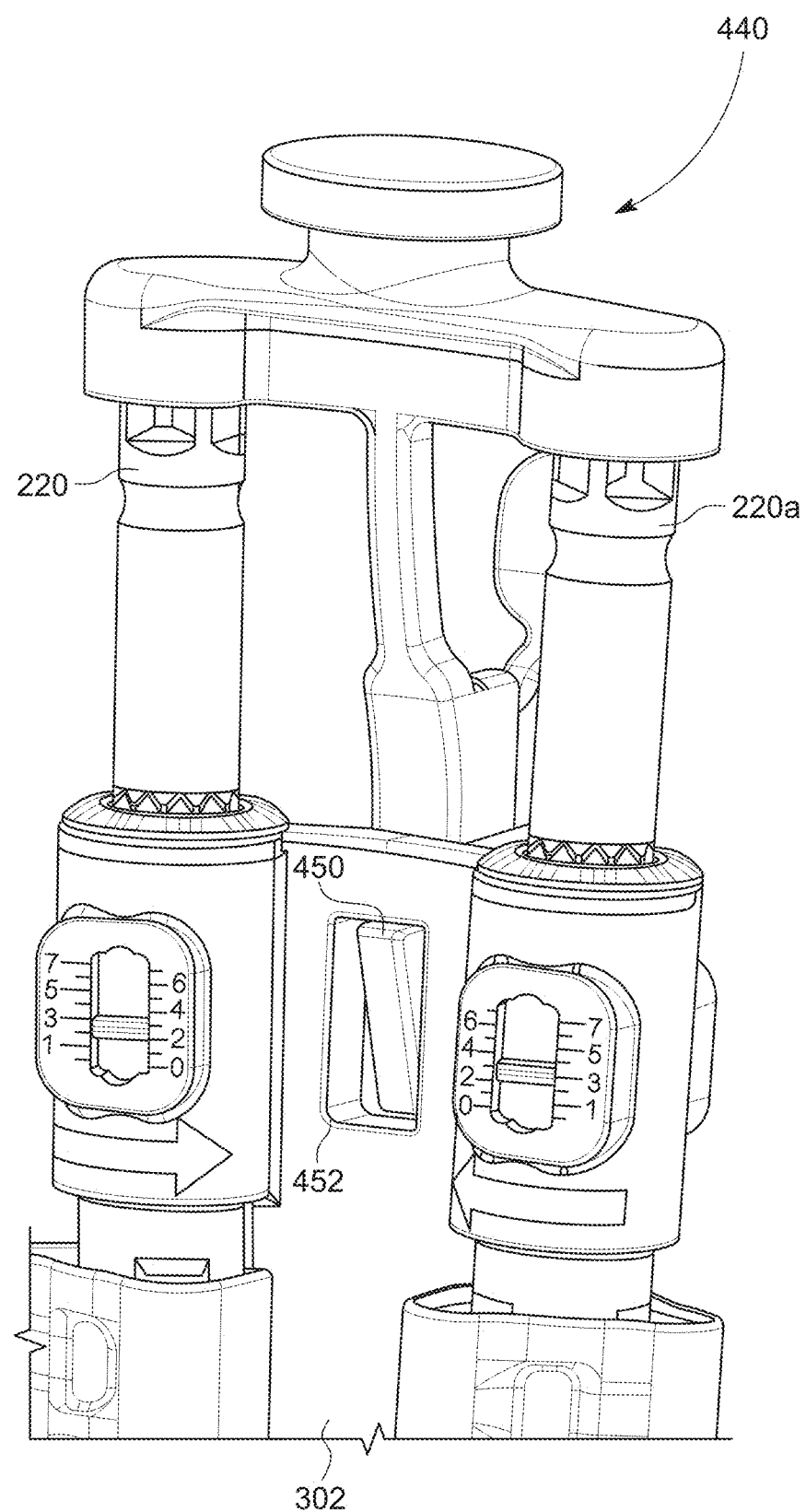
Figure 11F:
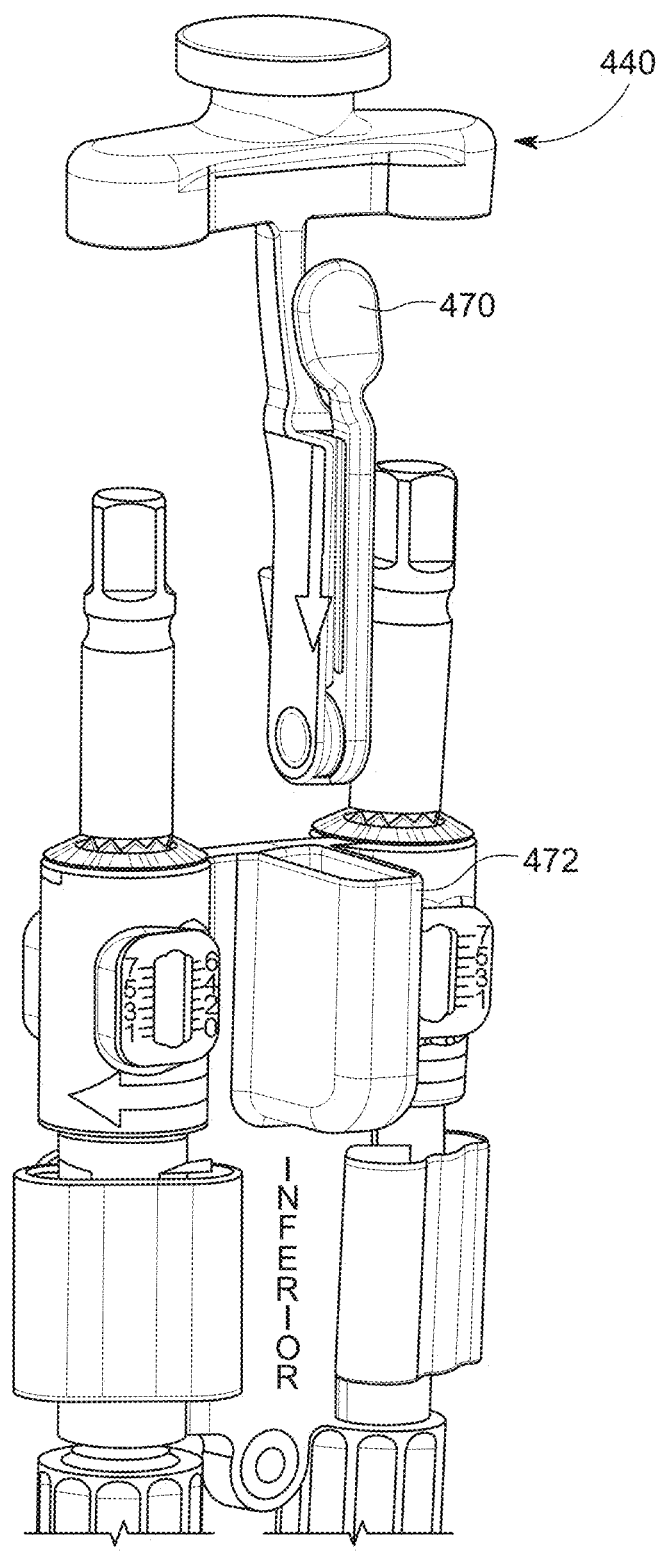

FIGS. 11D-11F show an example cap assembly according to embodiments of the disclosure. The example cap assembly 440 is similar to the cap assembly 340 shown in FIGS. 10A-10C in some aspects. For example, the cap assembly 440 comprises a first cap 442 and a second cap 444. The first and second caps 442, 444 are configured to couple with the first and second driving shafts 220, 220a respectively when the torqueing handles are removed. The first and second caps 442, 444 may include ribbed female features configured to fit over the male features on the first and second driving shafts 220, 220a to prohibit rotation of the first and second driving shafts when the cap assembly is attached. The example cap assembly 440 may further comprise a third cap 446 configured to receive an impaction force. The cap assembly 440 may be constructed from a metal such as stainless steel to allow the user to deliver an impaction force with e.g. a mallet and transfer a force down to the implant device to aid insertion of the implant device into the intervertebral disc space. The third cap 446 may have a geometry e.g. a circular disc with a neck, or any other suitable geometry to serve as a gripping point or site for connecting with a slap hammer to receive a pull-out force to remove the implant device out of or reposition the implant device in the intervertebral disc space. FIGS. 11D-11E depict the cap assembly 440 attached and secured to the instrument. FIG. 11F depicts the cap assembly 440 in attaching to or releasing from the instrument.

Figure 11G:
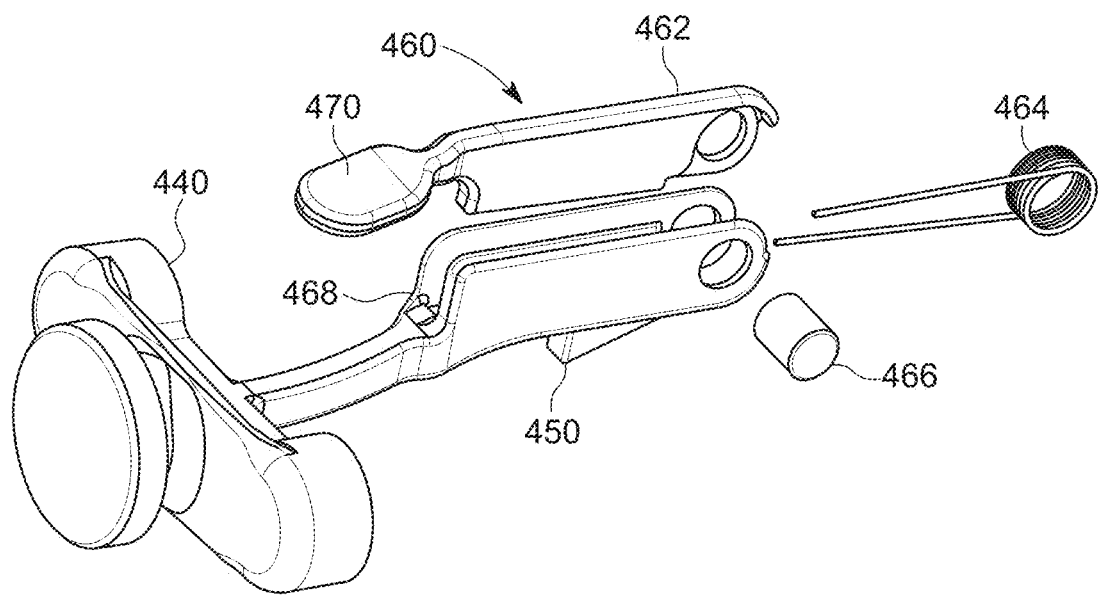
FIGS. 11G-11I depict an example lever release mechanism according to embodiments of the disclosure.
Figure 11H:
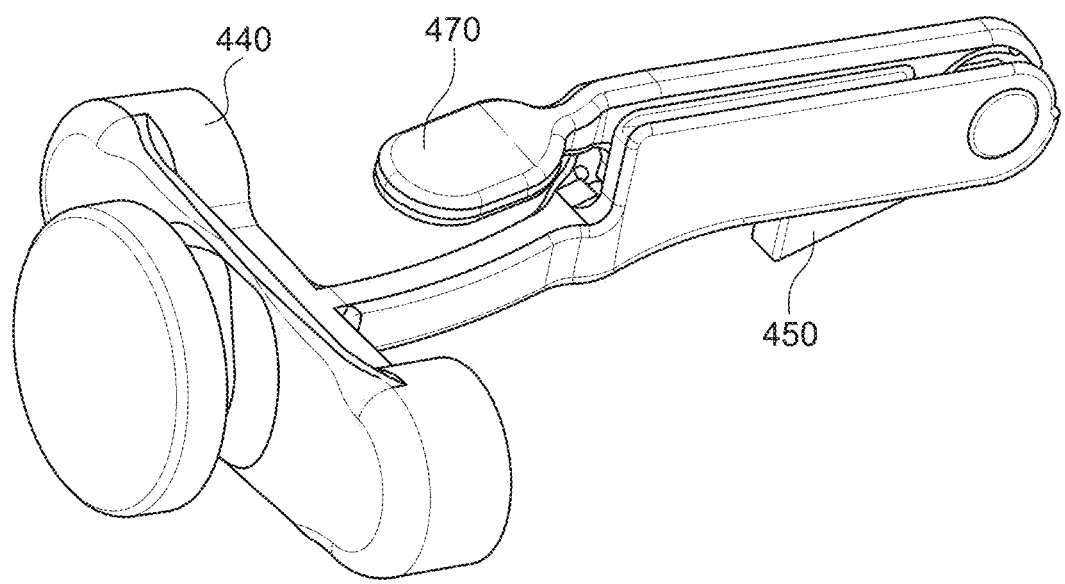
Figure 11I:
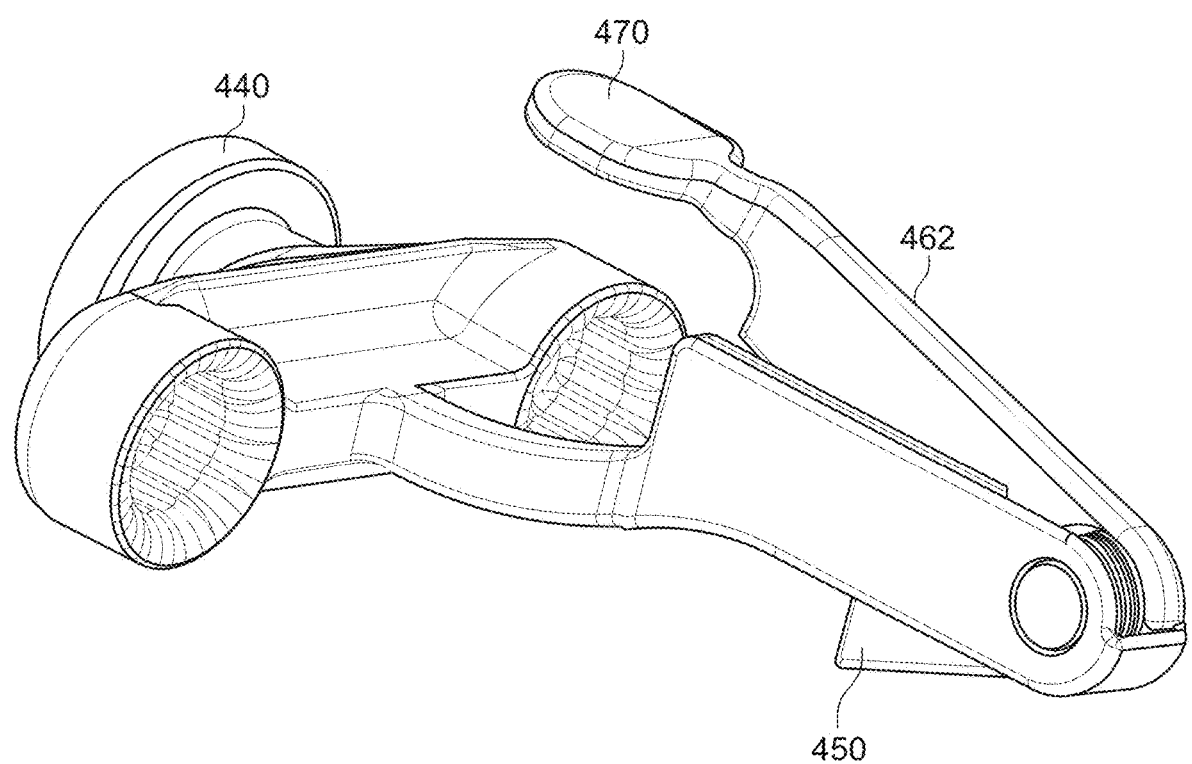

The cap assembly 440 may include a latch feature 450 configured to engage the chassis body 302 via a cut feature 452 in the chassis body 302 (FIG. 11E). The cap assembly 440 may be attached or secured to the instrument, or released from the instrument, by a lever release mechanism 460. As shown in FIGS. 11G-11I, an example lever release mechanism 460 includes a lever 462, a torsion spring 464, and a pin 466 that can fit through the hole features in the lever, torsion spring and the cap to hold the components together. The pin 466 may be welded or spot welded with the lever 462 to keep the entire cap release mechanism together while still allowing it to function properly. The pin 466 may rotate when the lever 462 is compressed towards or released away from the cap 440. When assembled, the lever release mechanism 460 may have a compressed state (FIG. 11H) wherein the lever is pushed in a slot feature 468 in the cap 440, and an expanded state (FIG. 11I) wherein the lever 462 is pulled out of the slot feature 468 and maintains extended due to the torsional resistance or torque provided by the torsion spring 464. The lever 462 may include a lever interface 470 that can be pinched by a user in compressing the lever towards or releasing it away from the cap 440.

In attaching the cap assembly 440 to the instrument (FIG. 11F), the user may compress the lever release mechanism 460 by pinching the lever interface 470 towards the cap 440. In the compressed state of the lever release mechanism 460, the cap assembly 440 can be inserted into a housing 472 on the chassis body. Once inside the housing 472, the user may expand the lever release mechanism 460 by pinching the lever interface 470 away the cap 440, allowing the latch feature 450 to hook the chassis body through the cut feature 452 (FIG. 11E). In the expanded state, the lever 462 may hold against the housing 472 via the torsion spring 464, allowing the latch 450 to hook the chassis body and keeping the cap assembly to be locked (FIG. 11D). To dis-attach the cap assembly 440 from the instrument, the user may compress the lever release mechanism 460 by pinching the lever interface 470 towards the cap 440, freeing up space inside the housing 472, thereby allowing the user to disengage the latch feature 450 from the chassis body 302 and pull the cap assembly 440 out of the housing 472.

Figure 11J:
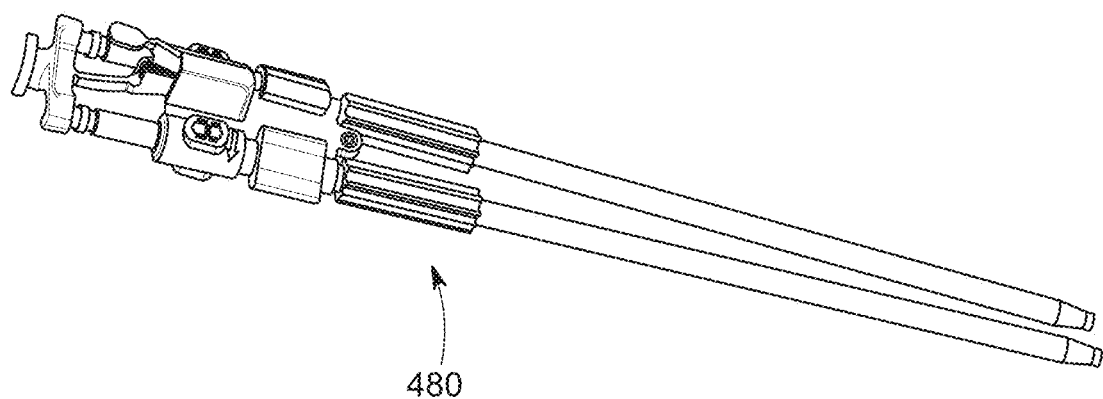
FIGS. 11J and 11K are perspective views of a surgical instrument including a cap assembly and a lever release mechanism shown in FIGS. 11D-11I.
Figure 11K:
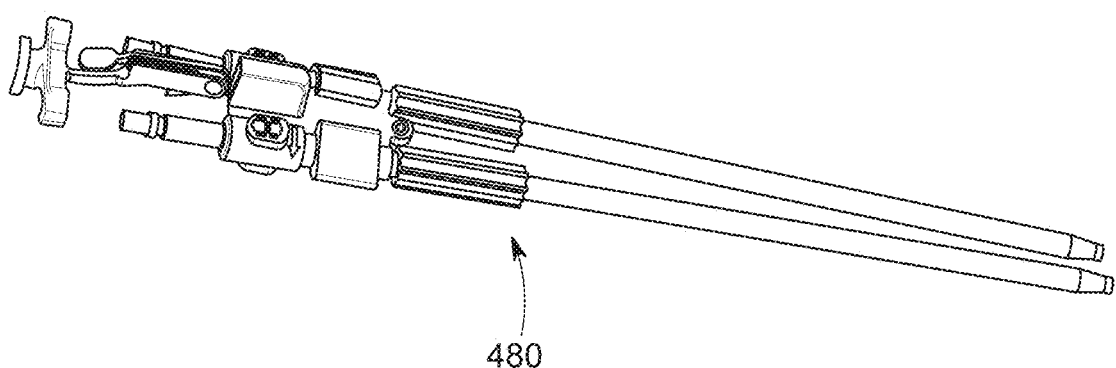

The lever release mechanism 460 shown in FIGS. 11D-11I simplifies the manufacturing by reducing assembly parts and provides a more intuitive and friendly interface for the user. For example, pinching the release interface 470 away from the instrument body allows the lever mechanism 460 to be expanded and thus allows the cap assembly 440 to be locked to the instrument, whereas pinching the release interface 470 toward the instrument body allows the lever mechanism 460 to be compressed and thus allows the cap assembly 440 to be released from the instrument. FIGS. 11J-11K show perspective views of a surgical instrument 480 including a cap assembly and a lever release mechanism in a lock and unlock position respectively.

With reference to FIGS. 12A-12E and FIGS. 1-2, the surgical instrument 200 may include a sleeve-release system 380 operable to lock or secure the first and second tubular sleeves 210, 210a to the chassis preventing the first and second tubular sleeves from dis-attaching from the chassis, and operable to unlock the first and second tubular sleeves 210, 210a to allow the first and second tubular sleeves to release or dis-attach from the chassis.

The sleeve-release system 380 may include a first sleeve-release assembly 382 and second sleeve-release assembly 382a. The first sleeve-release assembly 382 is slidable on the chassis and can be moved e.g. up or down by the user between a lock position and an unlock or release position (FIGS. 12D, 12E). At the lock position (FIG. 12D), the first tubular sleeve 210 is prevented from dis-attaching from the chassis 300 while being capable of freely rotating. At the lock position, the first tubular sleeve 210 is confined and prevented from wobbling while being allowed to rotate on a fixed axis. At the release position (FIG. 12E), the first tubular sleeve 210 can be dis-attached from the chassis 300 or pulled out by the user. Similarly, the second sleeve-release assembly 382a is slidable on the chassis 300 between a lock position and an unlock or release position. At the lock position, the second tubular sleeve 210a is prevented from dis-attaching from the chassis while being capable of freely rotating. At the lock position, the second tubular sleeve 210a is confined and prevented from wobbling while being allowed to rotate on a fixed axis. At the release position, the second tubular sleeve 210a can be dis-attached from the chassis or pulled out by the user.

Figure 12A:
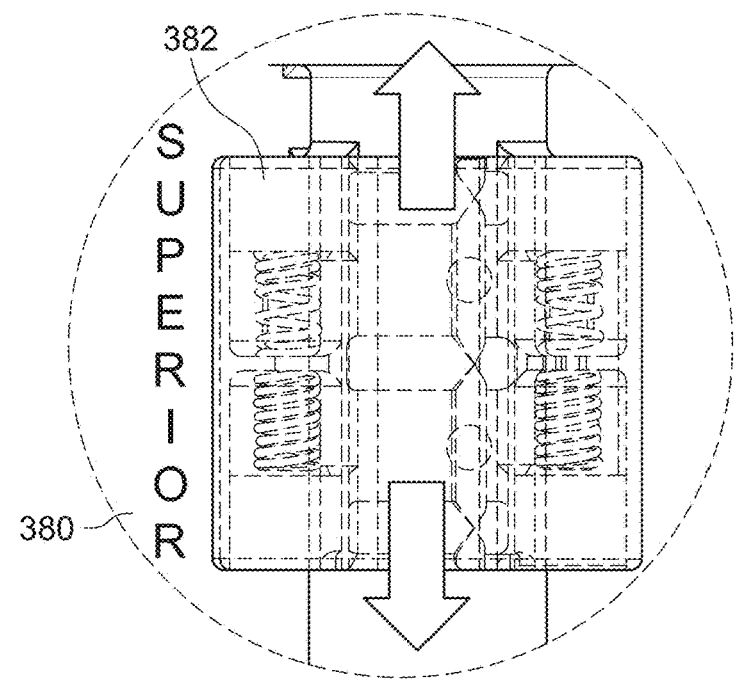
FIG. 12A depicts an example sleeve-release mechanism according to embodiments of the disclosure.
Figure 12B:
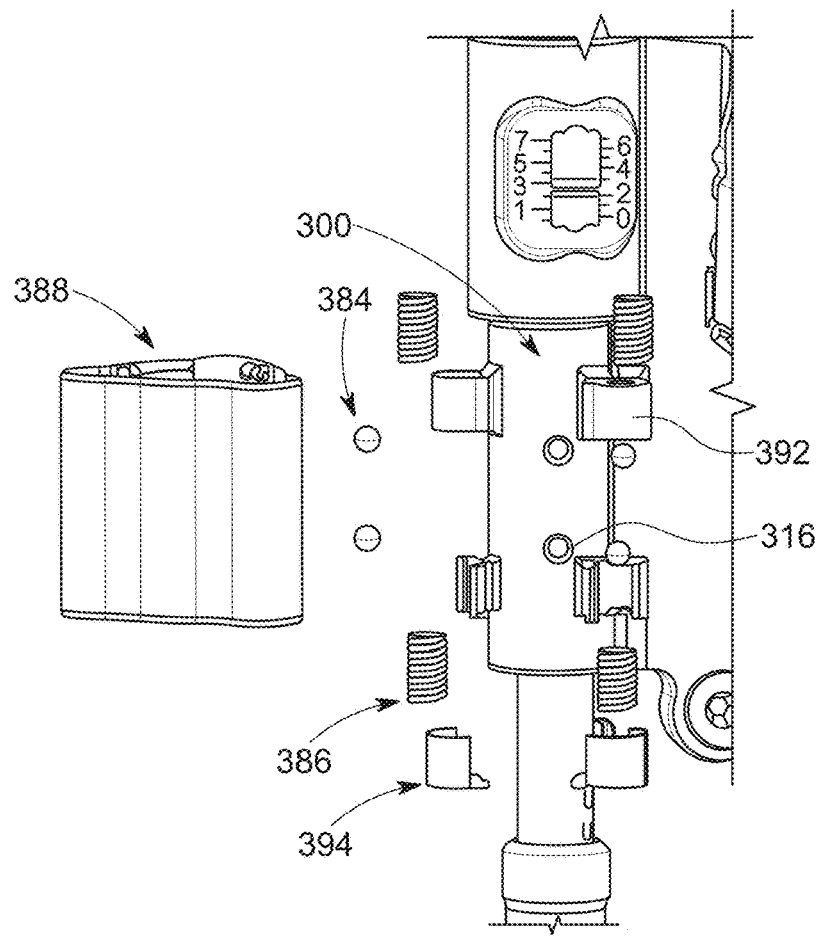
FIG. 12B shows an exploded view of the sleeve-release mechanism of FIG. 12A.
Figure 12C:
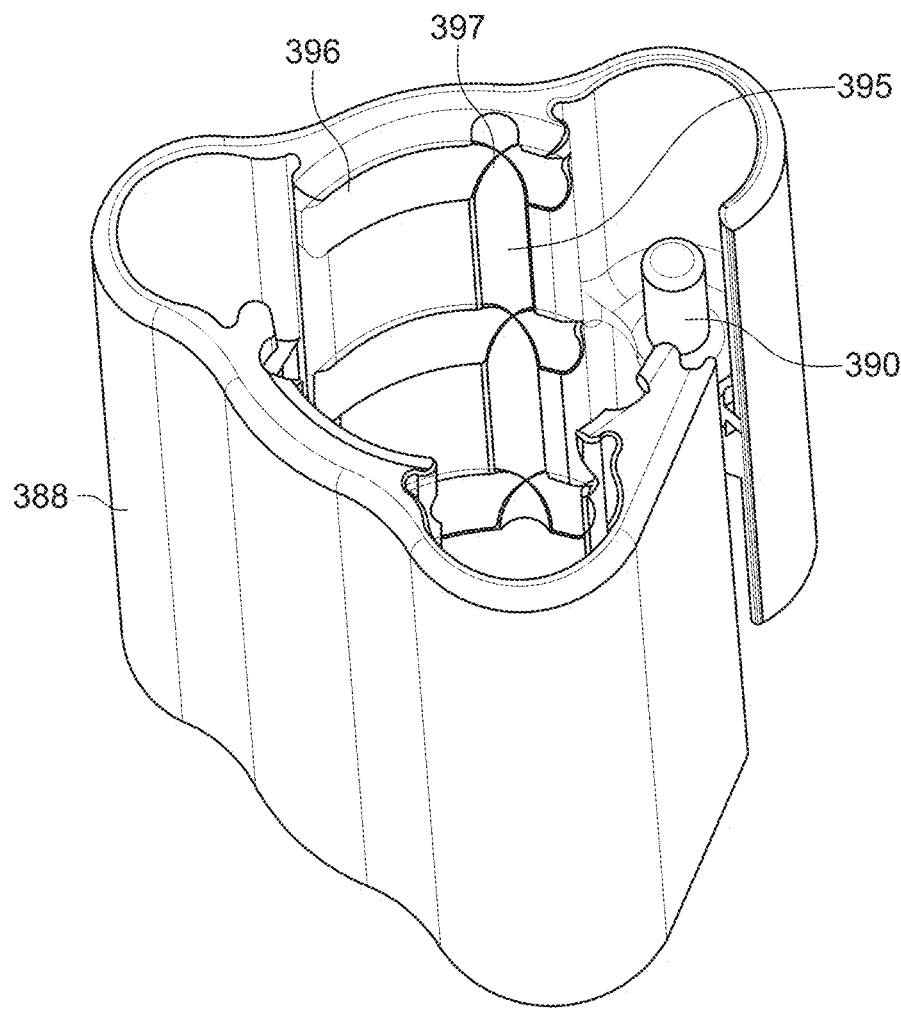
FIG. 12C is a top perspective view of an example release according to embodiments of the disclosure.
Figure 12E:
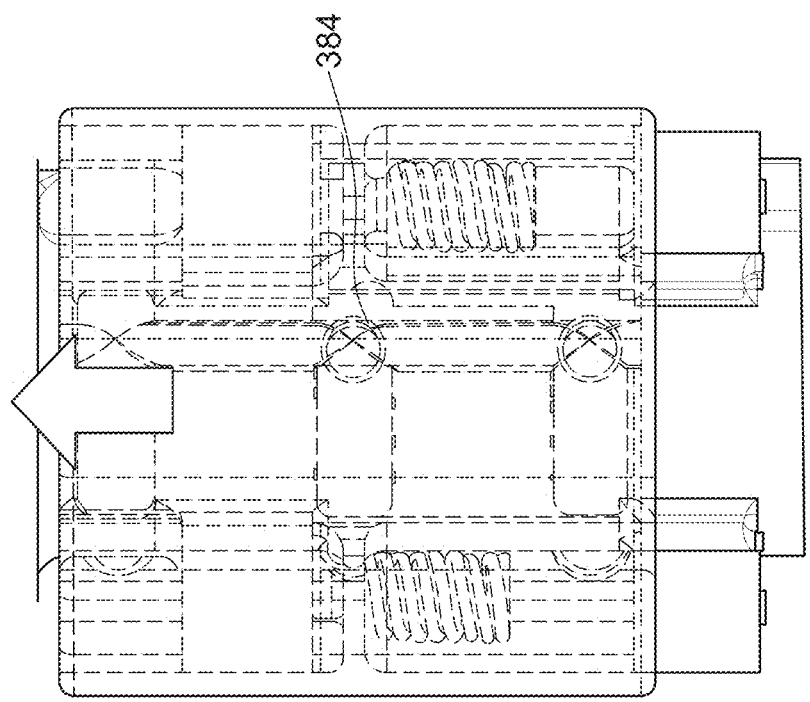
FIG. 12E depicts a release position of the sleeve-release mechanism.
Figure 12D:
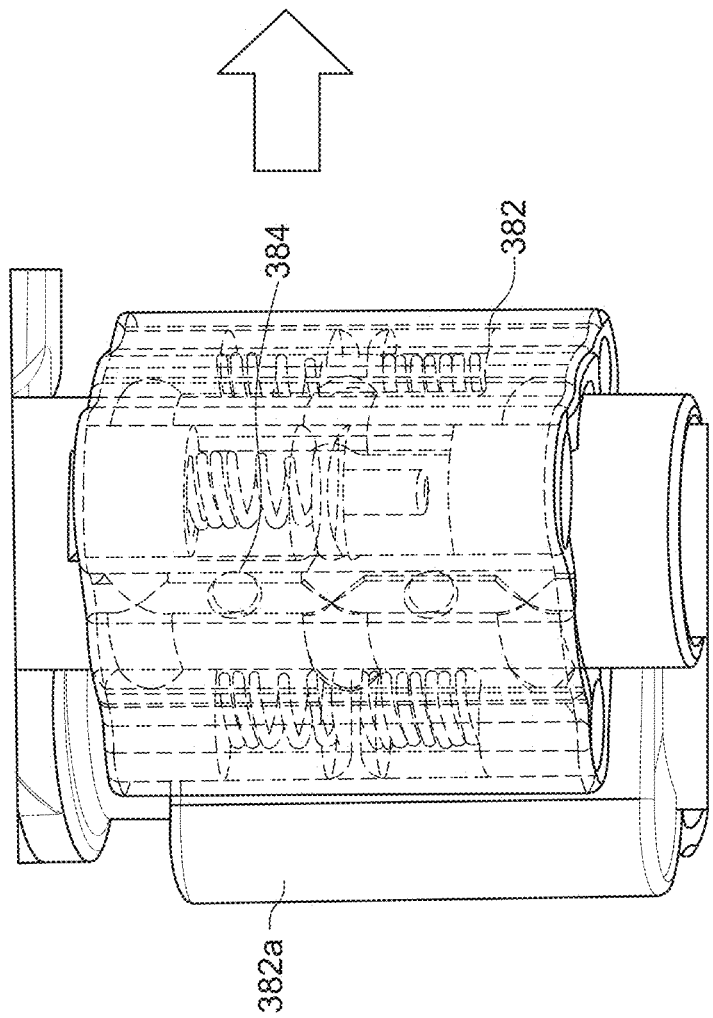
FIG. 12D depicts a lock position of the sleeve-release mechanism.

As shown in FIGS. 12A-12C, the example sleeve-release assembly 382 comprises ball bearings 384, compression springs 386, and a sleeve release 388 housing the ball bearings 384 and compression springs 386. The ball bearings 384 may be received in the ball bearing housing pockets 316 provided in the chassis 300, and interact with the release 388 when the release 388 is moved e.g. up or down or at a default position. The compression springs 386, which may be held on the posts 390 inside the release 388, allow the movement of the release, when being pulled up or down (e.g. to an unlock position), to spring back into a default place (e.g. the lock position). Retainers 392 and covers 394 may be provided on the chassis to further retain the compression springs. The internal surface of the release 388 is provided with grooves sized and shaped to interact with ball bearings 384. FIG. 12C shows an example release 388 provided with a vertical groove 395 and horizontal grooves 396. The vertical groove 395 and the horizontal grooves 396 intersect at points 397.

FIG. 12D shows an assembled view wherein the release is in a default or lock position. FIG. 12E shows an assembled view wherein the sleeve is pulled up to an unlock or release position. When the release is in the default lock position as shown in FIG. 12D, the release engages the ball bearings 384 in the vertical grooves. The ball bearings are held tight against the tubular sleeve in the chassis, preventing the tubular sleeve from being axially pulling out of the chassis. The ball bearings can spin in the vertical grooves, allowing the tubular sleeve to spin or rotate, thereby allowing the instrument to be connected with an implant device. When the sleeve is e.g. pulled up to an unlock position as shown in FIG. 12E, the ball bearings are placed in the intersections of the vertical and horizontal grooves. At the unlock position, the ball bearings in the intersections of the grooves are no longer held tight against the tubular sleeve, thereby allowing the tubular sleeve to be pulled out of the chassis. Similarly, when the release is pulled down to an unlock position, the ball bearings are placed in the intersections of the grooves where the ball bearings are no longer held tight against the tubular sleeve, thereby allowing the tubular sleeve to be pulled out of the chassis. The release may be restricted from moving to far up or down by the springs in their fully compressed state.

Figure 13B:
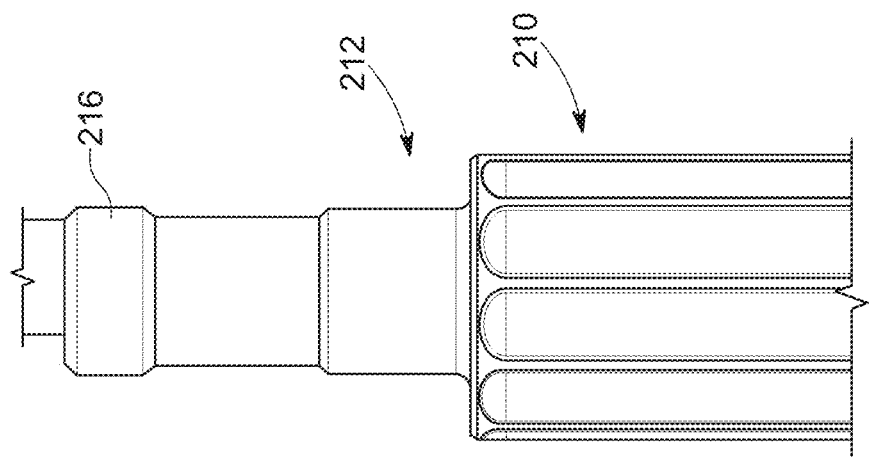
FIGS. 13A and 13B depict an end section of an example tubular sleeve according to embodiments of the disclosure.
Figure 13A:
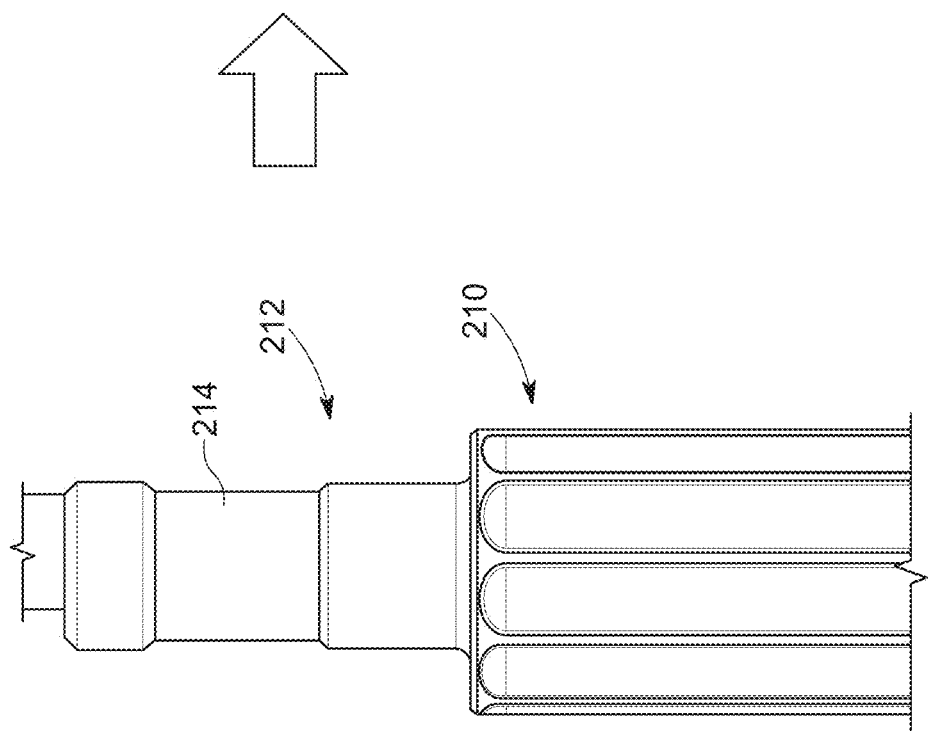

FIGS. 13A and 13B show an example tubular sleeve 210 having an end portion 212 configured to be attached to or dis-attached from the chassis using a sleeve-release assembly of the disclosure. The end portion 212 of the tubular sleeve has a section 214 with a reduced diameter. When the release is in the lock position (FIG. 12D), the ball bearings 384 are in contact with the section 214 with a reduced diameter. The small length of the section 214 of smaller diameter allows the tubular sleeve 210 to move axially in a small distance when the release in the lock position. The freedom of the tubular sleeve in an axial or in-and-out movement in a small distance allows one tubular sleeve to be fully connected to the implant device before the other tubular sleeve is connected. When the release is in an unlock position (FIG. 12E), the ball bearings 384 move into intersections of the grooves where the ball bearings can slide in and out of their pockets and move past the section 216 of the sleeve with a larger diameter, allowing the tubular sleeve be released.

Various embodiments of a surgical instrument and an interbody fusion system have been described. The surgical instrument allows adjustment of dual anatomical directions independently of one another. As such, each patient's unique anatomical spinal balance parameters can be met. This can lead to a quicker fusion in the patient's restored correct anatomical position along with less vertebral body subsidence into the spinal implant, which in turn provides a better quality of life for the patient with less pain.

Figure 17:
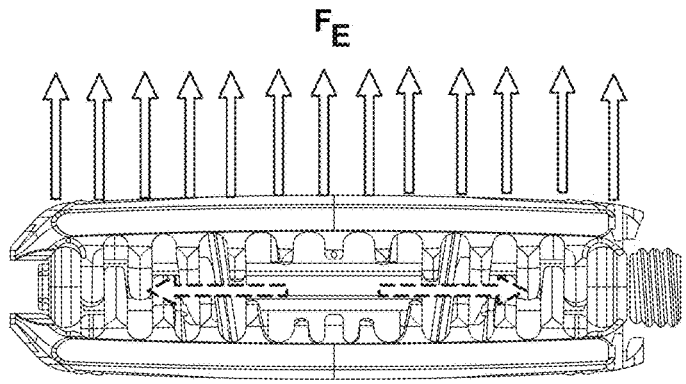
FIG. 17 illustrates creation of distraction forces by torqueing one or both rotatable features of an example implant device according to embodiments of the disclosure.
Figure 17:
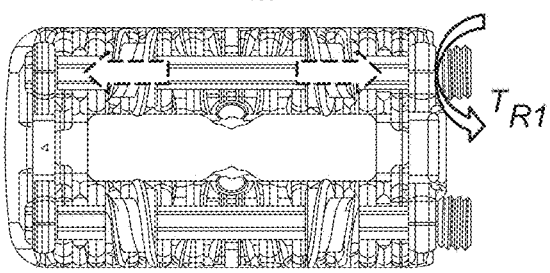
Figure 17:
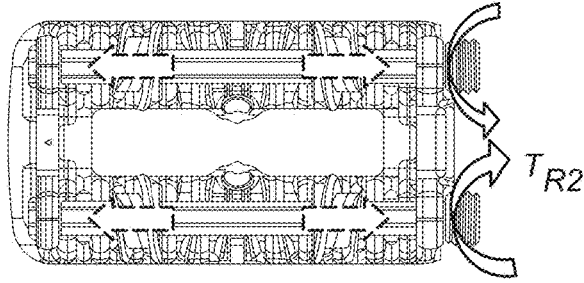
Figure 17:
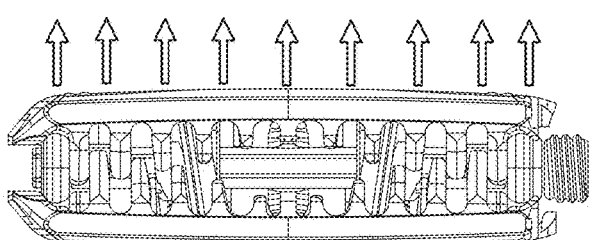
Figure 17:
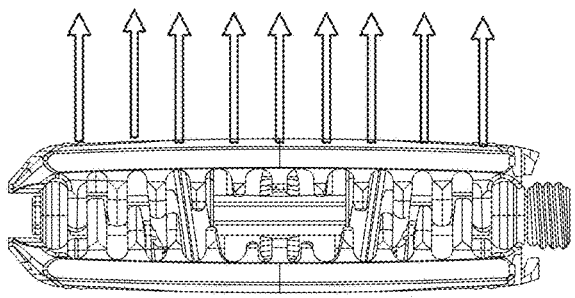

The surgical instrument of the disclosure allows a surgeon to distract an intervertebral disc space bi-directionally within a reference plane independently. This allows the surgeon to distract the intervertebral disc space that matches the patient's specific spinal balance by alternating reference directions to achieve the lordosis or kyphosis or by distracting both sides simultaneously. FIG. 17 illustrates distraction forces created by torqueing one rotatable feature of an implant device at a time and by torqueing both rotatable features simultaneously. The equations shown in FIG. 17 describe the relationship among the factors relating to the torque applied to implant device. In the equations, $T_R$ represents the torque applied to the driving shaft engaging the cam members of the implant device for expanding the shell members, $d_m$ represents the mean diameter of the tapered external helical threaded members, $F_E$ represents the distraction force or the load applied by the adjacent vertebral bodies, f represents the coefficient of friction of the working material, and l represents the lead or the pitch of the helical threading. As shown in FIG. 17, distracting the implant device by simultaneously torqueing both rotatable features of the implant device would double the distraction force as compared to distracting only one side at a time. The surgical instrument of the disclosure allows to create 8-9 mm of continuous distraction height of the intervertebral disc space within a single implant device, as compared to conventional systems which can only distract 5-7 mm of height within the intervertebral disc space with a single device.

The two independent indicator systems provided on the instrument allow the surgeon to have visual feedback of two adjustments or reference directions independently. The two independent indicator systems allow the surgeon to see two different heights in the different reference directions. Further the offset of height in the two different reference directions can provide the surgeon with a visual measure of the spinal balance such as lordosis, kyphosis, coronal offset etc.

The cap assembly of the instrument allows the surgeon to deliver an impaction and pull-out force when needed. Further, the cap assembly locks the driving elements from accidently rotating and delivering a torque to the implant device prior to insertion into the intervertebral disc space, or accidently providing a torque to the implant device upon removing the instrument from the implant device.

The sleeve-release system allows the surgeon to disconnect the tubular sleeves from the body of the instrument during operation if desired. This would allow for a better direct and fluoroscopic viewing down the working surgical hole to gain better visibility of the implant device. It also can provide a quick way to retrieve the implant device with just the sleeves if implant device needs to be removed. The sleeve-release mechanism allows the sleeves to be disattached from the body of the instrument after the surgery, allowing for a more thorough cleaning and/or sterilization of the instrument.

The surgical instrument of this disclosure can be used for inserting, removing, and operating a suitable implant device. Many configurations, variations, or options of the surgical instrument can be provided for use with different kinds of implant devices sized and shaped for placement in various regions of the patient's spine such as the lumbar, thoracic or cervical region of the spine via various approaches such as a lateral, anterior, or posterior approach. Therefore, as a treatment planning step, the surgeon may review the condition or problem of the damaged or degenerated discs of a patient which may have a particular physical size or built, determine a proper surgical approach to the targeted intervertebral disc space and the size of working access hole, and choose a configuration of the surgical instrument to accommodate the patient's preference and application. By way of example, a surgical instrument including a single torqueing handle and a cap assembly (FIGS. 2 and 5) can be provided as a standard offering for use with a lateral lumbar interbody fusion (LLIF) implant device. This option can provide independent anterior and posterior implant adjustment in an alternating manner. This option can be configured to be compatible with retractor blades up to e.g. 150 mm of length and 23 to 24 mm working access holes. As another example, a surgical instrument including two torqueing handles, a cap assembly, and optionally a driver adapter (FIGS. 3-5), can be provided to be used with an LLIF implant device for treating patients with extreme or severe degenerated vertebral discs. This option can provide independent anterior and posterior implant adjustment in a simultaneous or alternating manner, and allows for more distraction force if needed. This option can be configured to be compatible with any lengths of available retractor blades and 29-32 mm working access holes. It should be noted that the options of the instrument and their specific features or specifications are provided for illustration purpose. Various configurations and variations can be made to accommodate different user preferences and applications, and the claims of this disclosure are not limited by the specific options and specifications.

Once a desired surgical instrument is chosen, the instrument can be connected to the implant device. The surgical instrument can be connected to the implant device by rotating the tubular sleeves to allow e.g. the female threads in the end portions of the tubular sleeves to engage with the male threads on the driving mechanisms of the implant device (FIG. 7). Rotating the tubular sleeves in an opposite direction can dis-connect the instrument from the implant device. The tubular sleeves may be provided with features such as grips or the like for ease of rotating the tubular sleeves.

Figure 14A:
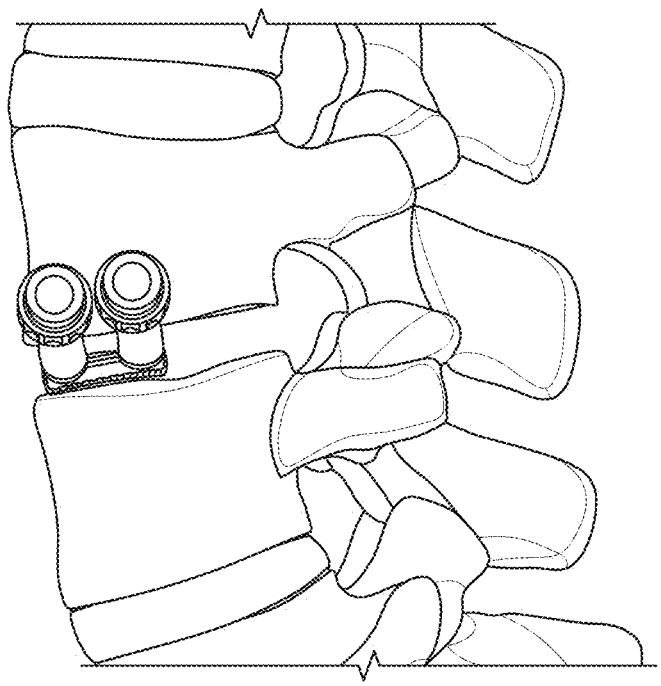
FIG. 14A is a sagittal view of adjacent vertebrae with an implant device being placed in the intervertebral disc space through a lateral approach in an anatomy of a patient according to embodiments of the disclosure.
Figure 14B:
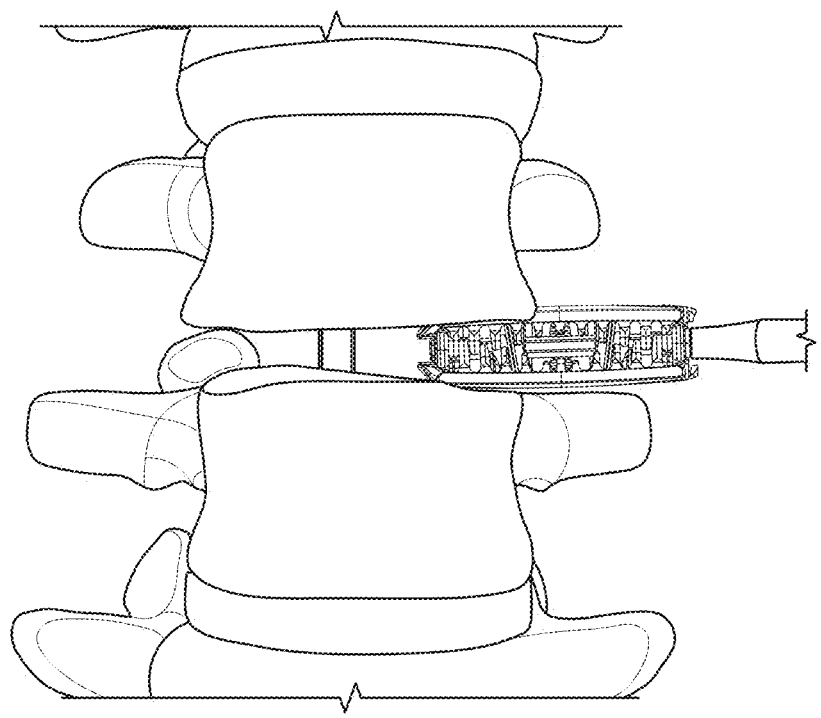
FIG. 14B is an anterior view of FIG. 14A.

Once connected to the surgical instrument, the implant device can be then inserted into the targeted intervertebral disc space. If needed, the cap assembly can be attached to the instrument and remained on during the insertion of the implant into the intervertebral disc space. The cap assembly can keep the implant device locked in its starting height configuration during insertion. If needed, a hammering force may be applied to the cap to aid the implant device to enter the intervertebral disc space (FIG. 10B). If needed, a pull-out force may be applied to the instrument e.g. by connecting a slap hammer to the cap gripping point to re-position or otherwise to pull out the implant device from the intervertebral disc space (FIG. 10C). FIGS. 14A-14B show an implant device inserted between adjacent vertebrae in the lumbar region of a patient's spine using a lateral approach. FIG. 14A is a sagittal view of the vertebrae and inserted device. FIG. 14B is an anterior view of the vertebrae and inserted device.

Once inserted into the intervertebral disc space, the cap assembly can be removed from the instrument using the cap ejector mechanism or lever release mechanism (FIGS. 11A-11K). A torqueing handle can then be connected to a driving shaft to distract the vertebrae and set the implant device to the patient's anatomy.

Figure 15A:
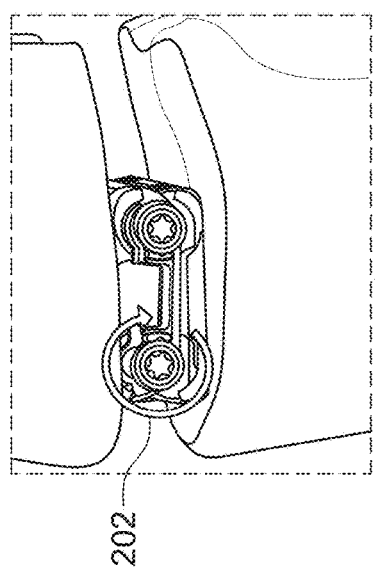
FIGS. 15A and 15B are sagittal views depicting operating methods according to embodiments of the disclosure.

With reference to FIG. 15A, a single torqueing handle 202 can be used in distracting the implant device. The torqueing handle 202 can apply torque to one of the driving shafts first, allowing torque to be transferred to one of the driving mechanisms of the implant device. Then, the torqueing handle 202 can be removed from the driving shaft and attached to the other driving shaft to apply torque, allowing toque to be transferred to the other driving mechanism of the implant device. Therefore, according to some embodiments of the disclosure, torque can be applied to the first and second driving mechanisms of an implant device alternatively and independently, allowing the amount of expansion and/or contraction of the implant device along the first lateral side to be independently and alternatively adjusted or controlled with respect to the amount of expansion and/or contraction of the implant device along the second lateral side of the implant.

Figure 15B:
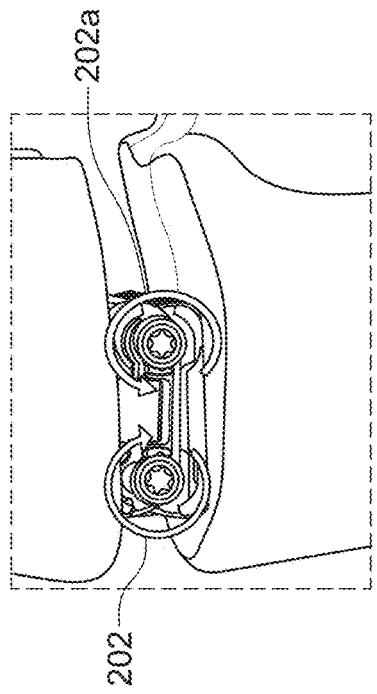

With reference to FIG. 15B, two torqueing handles 202, 202a can be provided in the instrument and used in distracting the implant device. The first handle 202 is used to torque the first driving shaft, allowing torque to be transferred to the first driving mechanism of the implant device. The second handle 202a is used to torque the second driving shaft, allowing torque to be transferred to the second driving mechanism of the implant device. If desired, an adapter can be coupled to one of the first and second driving shafts to offset the two torqueing handles to allow the surgeon to gain better grip while operating both handles. Therefore, according to some embodiments of the disclosure, torque can be applied to the first and second driving mechanisms of the implant device independently, allowing the amount of expansion and/or contraction of the implant device along the first lateral side to be independently adjusted or controlled with respect to the amount of expansion and/or contraction of the implant device along the second lateral side of the implant. The independent adjustment or control of the amount of expansion and/or contraction of the implant device along the first lateral side and the second lateral side of the implant can be conducted in a simultaneous manner by working the first and second torqueing handles 202, 202a simultaneously, or in an alternative manner by working the first and second torqueing handles 202, 202a alternatively or sequentially. As such, the first driving mechanism can be expanded to the same extent as the second driving mechanism, or to a greater or lesser extent than the second driving mechanism, thereby effecting expansion of the implant device from both the first and second lateral sides of the implant, and also effecting an angular tilt of the shell members relative to one another.

In the example shown in FIGS. 15A-15B, the implant device is inserted through a lateral approach in the anatomy of the patient. As such, when the implant device is positioned in the intervertebral disc space between the vertebrae, the first and second driving mechanisms of the implant device, or the first and second lateral sides of the implant device, are generally perpendicular to a sagittal plane of the patient. The expansion and/or contraction at the first and second lateral sides of the implant device would affect the patient's spinal balance or alignment in the sagittal plane. Alternatively, according some embodiments of the disclosure, the implant device is inserted through an anterior or posterior approach in the anatomy of the patient. As such, when the implant device is positioned in the intervertebral disc space between the vertebrae, the first and second driving mechanisms of the implant device, or the first and second lateral sides of the implant device, are generally perpendicular to a coronal plane of the patient. The expansion and/or contraction at the first and second lateral sides of the implant device would affect the patient's spinal balance or alignment in the coronal plane.

Figure 16A:
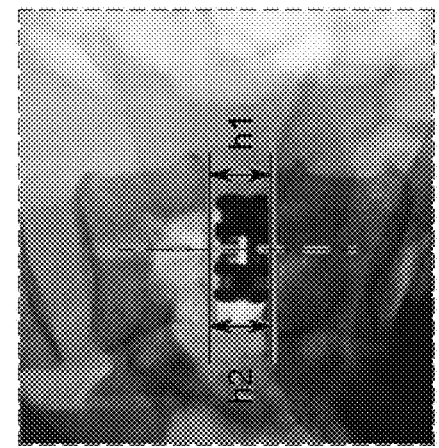
FIGS. 16A and 16B are x-ray images showing an example implant device placed in an intervertebral disc space according to embodiments of the disclosure.
Figure 16B:
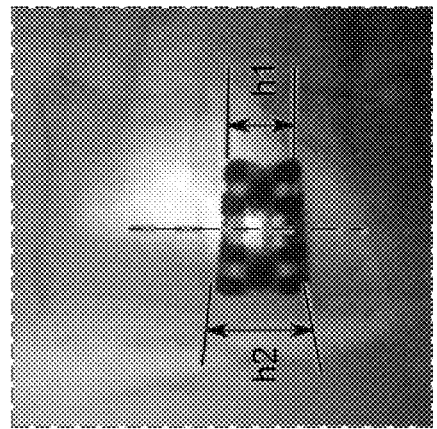

Once all desired adjustments have been made, the surgeon may view the measuring schemes on the instrument to determine the height and/or lordosis or kyphosis added to the implant device to match the patient's unique spinal balance requirements. The two independent indicator systems on the instrument allow the surgeon to have visual feedback of two adjustments or reference directions independently. The two independent indicator systems allow the surgeon to see two different heights in the different reference directions. Further the offset of height in the two different reference directions can provide the surgeon with a visual measure of spinal balance such as lordosis, kyphosis, coronal offset etc. (FIGS. 16A-16B). Therefore, direct measurement feedback during surgery can be provided by using the surgical instrument of this disclosure.

Once the surgeon has made all the necessary adjustments to the spinal implant device and has the desired final configuration, the torqueing handles can be removed, and the cap is placed back on over the driving shafts. This ensures that the implant device remains in its final configuration when the surgical instrument is disconnected. The surgical instrument can be removed from the implant device by rotating the tubular sleeves.

Some surgeon may prefer to remove the chassis of the instrument from the tubular sleeves to provide them with better fluoroscopic and direct visualization of the implant device in the patient's body during surgery. This can be achieved by using the sleeve-release mechanisms as described above. If the implant device needs to be retrieved following a configuration or in a secondary surgery, the implant can be quickly and easily connected to the sleeves of the surgical instrument to retrieve the implant. A slap-hammer can be connected to the instrument if a pull-out force is needed to aid the removal of the implant.

After the surgery, the sleeves can be removed from the instrument to allow for hospital technical personnel to perform a more thorough cleaning and/or sterilization procedure on the device if needed.

Various embodiments are described with reference to the figures. It should be noted that some figures are not necessarily drawn to scale. The figures are only intended to facilitate the description of specific embodiments and are not intended as an exhaustive description or as a limitation on the scope of the disclosure. Further, in the figures and description, specific details may be set forth in order to provide a thorough understanding of the disclosure. It will be apparent to one of ordinary skill in the art that some of these specific details may not be employed to practice embodiments of the disclosure. In other instances, well known components may not be shown or described in detail in order to avoid unnecessarily obscuring embodiments of the disclosure.

All technical and scientific terms used herein have the meaning as commonly understood by one of ordinary skill in the art unless specifically defined otherwise. As used in the description and appended claims, the singular forms of "a," "an," and "the" include plural references unless the context clearly dictates otherwise. The term "or" refers to a nonexclusive "or" unless the context clearly dictates otherwise.

Those skilled in the art will appreciate that various other modifications may be made. All these or other variations and modifications are contemplated by the inventors and within the scope of the invention.

What is claimed is:

1. A method, comprising:
    providing a spinal interbody fusion system comprising an implant device and an insertion tool, wherein the implant device comprises a housing, a first driving mechanism and a second driving mechanism each being operable to expand and/or contract the housing along a first lateral side and a second lateral side of the housing respectively, and the insertion tool comprises a chassis defining a first channel and a second channel, a first driving shaft received in the first channel, a second driving shaft received in the second channel, a first measuring system configured to measure a rotational movement of the first driving shaft in the first channel, a second measuring system configured to measure a rotational movement of the second driving shaft in the second channel, wherein each of the first driving shaft and the second driving shaft is independently and separately rotatable in the first channel and the second channel respectively;

connecting the insertion tool with the implant device;

inserting the implant device between adjacent vertebrae in a patient;

applying torque to the first and second driving mechanisms of the implant device independently using the first driving shaft and the second driving shaft via the first and second channels of the insertion tool respectively, whereby an amount of expansion and/or contraction of the housing along the first lateral side is independently adjusted relative to an amount of expansion and/or contraction of the housing along the second lateral side, the torque applied to the first and second driving mechanisms of the implant device being measured by the first and second measuring systems respectively.

2. The method of claim 1, wherein the applying of torque comprises applying torque with the first driving shaft to the first driving mechanism of the implant device via the first channel of the insertion tool simultaneously with and independently of applying torque with the second driving shaft to the second driving mechanism via the second channel of the insertion tool.

3. The method of claim 1, wherein the applying of torque comprises applying torque with the first driving shaft to the first driving mechanism of the implant device via the first channel of the insertion tool alternatively with and independent of applying torque with the second driving shaft to the second driving mechanism via the second channel of the insertion tool.

4. The method of claim 1, wherein the inserting of the implant device is carried out through a lateral approach in an anatomy of the patient, thereby when the implant device is positioned between the adjacent vertebrae, the first and second lateral sides of the housing of the implant device are generally perpendicular to a sagittal plane of the patient, and the expansion and/or contraction along the first and second lateral sides of the housing of the implant device affect the patient's spinal balance or alignment in the sagittal plane.

5. The method of claim 1, wherein the inserting of the implant device is carried out through an anterior approach or a posterior approach in an anatomy of the patient, thereby when the implant device is positioned between the adjacent vertebral bodies, the first and second lateral sides of the housing of the implant device are generally perpendicular to a coronal plane of the patient, and the expansion and/or contraction along the first and second lateral sides of the housing of the implant device affect the patient's spinal balance or alignment in the coronal plane.

6. The method of claim 1, wherein the first measuring system is configured to transfer a rotational movement of the first driving shaft into a linear movement, measure the linear movement, and provide an indication corresponding to cumulative rotations of the first driving shaft in the first channel, and the second measuring system is configured to transfer a rotational movement of the second driving shaft into a linear movement, measure the linear movement, and provide an indication corresponding to cumulative rotations of the second driving shaft in the second channel.

7. The method of claim 1, wherein the insertion tool comprises a first tubular sleeve releasably attached to the first channel of the chassis and a second tubular sleeve releasably attached to the second channel of the chassis.

8. A method, comprising:

providing a spinal interbody fusion system comprising an implant device and an insertion tool, wherein the implant device comprises a housing, a first driving mechanism and a second driving mechanism each being operable to expand and/or contract the housing along a first lateral side and a second lateral side of the housing respectively;

connecting the insertion tool with the implant device;

inserting the implant device between adjacent vertebrae in a patient; and applying torque to the first and second driving mechanisms of the implant device independently via the insertion tool, whereby an amount of expansion and/or contraction of the housing along the first lateral side is independently adjusted relative to an amount of expansion and/or contraction of the housing along the second lateral side, wherein the insertion tool comprises a chassis defining a first channel and a second channel, and a first driving shaft, and wherein the applying of torque comprises inserting the first driving shaft to the first channel, applying torque with the first driving shaft to the first driving mechanism via the first channel of the insertion tool, withdrawing the first driving shaft from the first channel, inserting the first driving shaft to the second channel, and applying torque with the first driving shaft to the second driving mechanism of the implant device via the second channel of the insertion tool.

9. The method of claim 8, wherein the insertion tool comprises a first measuring system configured to measure a rotational movement of the first driving shaft in the first channel, a second measuring system configured to measure a rotational movement of the first driving shaft in the second channel, and wherein the torque applied with the first driving shaft to the first and second driving mechanisms of the implant device is measured by the first and second measuring systems of the insertion tool respectively.

10. The method of claim 9, wherein the first measuring system is configured to transfer a rotational movement of the first driving shaft into a linear movement, measure the linear movement, and provide an indication corresponding to cumulative rotations of the first driving shaft in the first channel, and the second measuring system is configured to transfer a rotational movement of the first driving shaft into a linear movement, measure the linear movement, and provide an indication corresponding to cumulative rotations of the first driving shaft in the second channel.

* * * * *